United States Patent
Curtis

(10) Patent No.: US 6,787,345 B1
(45) Date of Patent: Sep. 7, 2004

(54) 55053, A NOVEL HUMAN EUKARYOTIC KINASE AND USES THEREFOR

(75) Inventor: Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/003,690

(22) Filed: Nov. 15, 2001

Related U.S. Application Data

(60) Provisional application No. 60/248,893, filed on Nov. 15, 2000.

(51) Int. Cl.[7] .......................... C12N 9/12; C12N 15/00; C12N 5/00; C12N 1/20; C07H 21/04
(52) U.S. Cl. .................... 435/194; 435/320.1; 435/325; 435/6; 435/252.3; 536/23.2
(58) Field of Search ............................. 435/194, 252.3, 435/6, 320.1, 325; 536/23.2, 23.1

(56) References Cited

FOREIGN PATENT DOCUMENTS

| WO | WO 01/38503 A2 | 5/2001 |
|---|---|---|
| WO | WO 01/96547 A2 | 12/2001 |

OTHER PUBLICATIONS

Database PIR–73, Accession No. S37928, May 1994.*

* cited by examiner

*Primary Examiner*—Maryam Monshipouri
(74) *Attorney, Agent, or Firm*—Millennium Pharmaceuticals Inc.

(57) ABSTRACT

The invention provides isolated nucleic acids molecules, designated EPK-55053 nucleic acid molecules, which encode novel protein kinase polypeptides. The invention also provides antisense nucleic acid molecules, recombinant expression vectors containing EPK-55053 nucleic acid molecules, host cells into which the expression vectors have been introduced, and nonhuman transgenic animals in which an EPK-55053 gene has been introduced or disrupted. The invention still further provides isolated EPK-55053 proteins, fusion proteins, antigenic peptides and anti-EPK-55053 antibodies. Diagnostic, screening, and therapeutic methods utilizing compositions of the invention are also provided.

8 Claims, 12 Drawing Sheets

FIG. 1A

Input file Fbh55053e.seq;Output File 55053.trans
Sequence length 2862

```
                                GTCGACCCACGCGTCCGCGACGCGTGGGCGACGCGTGGGCGG
                                                M   S   S   G   A   K   E   G   G       9
ACGCGTCCGGGGGGACCGGTCGGGGCCGGGGACCAAGGGCACC    ATG TCG TCC GGG GCC AAG GAG GGA GGT      27

G   G   S   P   A   Y   H   L   P   H   P   H   P   P   H   P   Q   H   A   Q          29
GGG GGC TCT CCC GCC TAC CAC CTC CCC CAC CCC CAC CCC CCA CAC CCC CAG CAC GCC CAA         87

Y   V   G   P   P   R   L   E   K   T   L   G   K   G   Q   T   G   L   V   K          49
TAT GTG GGC CCC TAT CGG GAG AAG ACG CTG GGC AAA CAG ACA GGG CTG GTT AAA                 147

L   G   V   H   C   H   I   T   G   Q   K   V   A   I   K   I   V   N   R   E   K      69
CTC GGG GTC CAC TGC CAC ATC ACG GGT CAG AAG GTC GCC ATC AAG ATC GTG AAC CGG GAG AAG     207

L   S   E   S   V   L   M   K   V   E   R   E   I   A   I   L   K   L   I   E          89
CTG TCG GAG TCG GTG CTG ATG AAG GTG GAG CGG GAG ATC GCC ATC CTG AAG CTC ATC GAA         267

H   P   H   V   V   L   S   H   L   H   D   V   Y   D   Y   K   N   K   Y   L   V     109
CAC CCA CAT GTC GTC CTC TCG CAC CTC CAC GAC GTC TAC GAC TAC AAG AAC AAG TAT TTG GTT     327

L   E   H   V   S   G   G   E   L   F   D   Y   L   V   K   G   R   L   T             129
CTG GAG CAC GTC TCG GGG GGT GAG CTA TTC GAC TAC CTG GTA AAG GGG AGA CTG ACG             387

P   K   E   A   R   K   F   F   R   Q   I   V   S   A   L   D   F   C   H   S         149
CCC AAG GAG GCC CGA AAG TTC TTC CGC CAG ATT GTG TCT GCG CTG GAC TTC TGC CAC AGC         447
```

FIG. 1B

```
  Y   S   I   C   H   R   D   L   K   P   E   N   L   L   D   E   K   N   N         169
 TAC TCC ATC TGC CAC AGA GAC CTA AAG CCC GAG AAC CTG CTT GAT GAG AAA AAC AAC         507

I   R   I   A   D   F   G   M   A   S   L   Q   V   G   L   D   S   L   E   T     189
 ATC CGC ATT GCA GAC TTC GGC ATG GCG TCC CTG CAG GTG GGG GAC AGC CTC GAG ACC         567

S   C   G   S   P   H   Y   A   C   P   E   V   I   F   A   G   E   K   D   G     209
 AGC TGC GGG TCC CCC CAT TAT GCG TGT CCA GAG GTG ATT TTC GCC GAA AAG GAT GGC         627

R   R   A   D   M   W   S   C   G   V   L   L   E   A   L   V   G   A   L         229
 CGC CGG GCA GAC ATG TGG AGC TGT GGA GTC CTG CTC GAG GCC CTG GTG GGG GCT CTG         687

P   F   D   D   N   L   R   Q   L   E   K   V   R   G   V   F   H         249
 CCC TTT GAT GAC AAC CTC CGC CAG CTG GAG AAG GTG CGG GGC GTC TTC CAC         747

M   P   H   F   I   P   D   C   Q   S   L   R   G   M   I   E   V   E         269
 ATG CCC CAC TTC ATT CCT GAT TGC CAG AGC CTC AGG GGA ATC ATC GAA GTG GAG         807

P   E   K   R   L   S   Q   I   E   L   H   P   W   Y   L   G   G   K         289
 CCC GAA AAA AGG CTC AGT CAG ATT CAG CAT CCT TGG TAC CTA GGC GGG AAA         867

H   E   P   D   P   C   L   E   P   A   P   G   R   R   V   A   M   R   S   L     309
 CAC GAG CCA GAC CCG TGC CTG GAG CCT GCC CGG CGG GTA GCC ATG CGG AGC CTG         927

P   S   N   G   E   L   D   P   V   L   E   S   M   A   S   L   G   C   F       329
 CCA TCC AAC GGA GAG CTG GAC CCC GTC CTA GAG AGC ATG GCA TCA CTG GGC TGC TTC       987
```

FIG. 1C

```
      R   D   R   E   R   L   H   R   E   L   R   S   E   E   E   N   Q   E   K   M   349
   AGG GAC CGC GAG AGG CTG CAT CGC GAG CTG CGC AGT GAG GAG GAG AAC CAA GAA AAG ATG  1047

I   Y   Y   L   L   L   D   R   K   E   R   Y   P   S   C   E   Q   Q   D   L   369
   ATA TAT TAT CTG CTT TTG GAT CGG AAG GAG CGG TAT CCC AGC TGT GAG CAG CAG GAC CTG  1107

P   P   R   N   D   V   D   P   R   K   S   M   P   S   D   S   P   M   L   R   389
   CCT CCC AAT GAT GTT GAC CCC CGG AAG TCT ATG CCC TCT GAT TCT CCC ATG CTG AGC CGT  1167

H   G   K   R   P   V   P   E   R   K   S   M   E   V   L   R   A   Q   H   G   409
   CAC GGG AAG CGG CCA GTT CCA GAG CGG AAG TCC ATG GAA GTC CTG CGG GCC CAG CAC GGG  1227

G   G   S   P   V   P   T   R   G   S   L   E   M   A   Q   H   S   Q   R   G   429
   GGT GGC TCC CCT GTA CCC ACC CGA GGC TCC TTG GAG ATG GCC CAG CAC AGC CAG CGA GGG  1287

S   R   S   V   G   A   S   R   T   G   L   S   S   P   L   S   P   R   G   R   449
   TCC CGT AGC GTC AGT GCC TCC ACG GGT CTG TCC TCC CCT CTA AGC CCA AGG GGG AGG AGG  1347

S   P   V   F   S   F   T   Q   S   P   E   P   G   A   D   E   A   R   G   G   469
   AGT CCG GTC TTT TCC TCA CCC GAG CCT GGA GAT GAG GCT CGA GGG GGG GGG GGG GGG GGC  1407

S   P   T   S   K   T   Q   R   S   P   T   L   P   S   R   P   R   G   A   G   489
   TCC CCG ACT TCC AAA ACG CAG CGC CCT CTG CTG CCT TCT CGG AGG CCC AGG GGT GCC GGG  1467

E   Q   P   P   P   S   S   A   R   S   T   P   L   P   G   P   P   S   P   P   509
   GAG CAG CCG CCC CCC AGT GCC CGC TCC ACA CCC CTG CCC GGC CCA CCC TCC CCG CCG CCG  1527
```

FIG. 1D

```
  R   S   G   G   T   P   L   H   S   P   L   H   T   P   R   A   S   P   T        529
CGC TCC TCT GGC GGG ACC CCC TTG CAC TCG CCT TTG CAC ACG CCC CGG GCC AGT CCC ACC    1587

G   T   P   G   T   T   P   P   P   S   P   P   V   G   G   G   A   A   W        549
GGG ACC CCG GGG ACA ACA CCA CCC CCC AGC CCC GGC GTC GGT GGC GGA GCC GCC TGG        1647

R   S   R   L   N   S   I   R   N   S   F   L   G   S   P   R   F   H   R        569
AGG AGT CGT CTC AAC TCC ATC CGC AAC AGC TTC CTG GGC TCC CCT CGC TTT CAC CGC        1707

K   M   Q   V   P   T   A   E   E   M   S   L   G   S   L   T   P   E   S        589
AAG ATG CAG GTC CCT ACC GCT GAG GAG ATG TCC AGC TTG GGC TCC CCA ACG GAG TCC        1767

L   A   K   R   S   W   F   G   N   F   I   S   L   D   K   E   E   Q   I   F    609
CTG GCA AAA CGC TCC TGG TTC GGG AAC TTC ATC TCC TTG GAC AAA GAA CAA ATA TTC        1827

L   V   L   K   D   K   P   L   S   I   K   A   D   I   V   H   A   F   L        629
CTC GTG CTA AAG GAC AAG CCT CTC AGC ATC AAA GCA GAC ATC GTC CAT GCC TTT CTG        1887

S   I   P   S   S   L   H   S   V   L   S   Q   T   S   F   R   A   E   Y   K    649
TCG ATC CCC AGC CTG AGT CAC AGT GTG CTG TCA CAG ACC AGC TTC AGG GCC GAG TAC AAG    1947

A   S   G   G   P   S   V   F   Q   F   Q   V   R   F   Q   D   I   S          669
GCC AGT GGC GGC CCC TCC GTC TTC CAA GTG CGC TTC CAG GTG GAC ATC AGC TCC            2007

S   E   G   P   E   P   S   P   R   D   G   S   G   G   G   I   Y   S          689
TCT GAG GGT CCA GAG CCC TCC CCG CGA CGG GAC GGC AGC GGA GGT GGC ATC TAC TCC        2067
```

FIG. 1E

```
      V   T   F   T   L   I   S   G   P   S   R   R   F   K   R   V   V   E   T   I   709
      GTC ACC TTC ACT CTC ATC TCG GGT CCC AGC CGT CGG TTC AAG CGA GTG GTG GAG ACC ATC 2127

Q   A   Q   L   L   S   T   H   D   Q   P   S   V   Q   A   L   A   D   E   K   729
      CAG GCA CAG CTC CTG AGC ACT CAT GAC CAG CCC TCC GTG CAG GCC CTG GCA GAC GAG AAG 2187

N   G   A   Q   T   R   P   A   G   A   P   R   S   L   Q   P   P   P   G   749
      AAC GGG GCC CAG ACC CGG CCT GCT GGT GCC CCA CGA AGC CTG CAG CCC CCA CCC GGC 2247

R   P   D   P   E   L   S   S   S   P   R   G   P   D   K   K   L   769
      CGC CCA GAC CCA GAG CTG AGC AGC AGC TCT CCC CGC CGA GGC CCC AAG GAC AAG AAG CTC 2307

L   A   T   N   G   T   P   L   P   *                                        779
      CTG GCC ACC AAC GGG ACC CCT CTG CCC TGA                                       2337

CCCACGGGGCCGGGGAGGGAGGGAGGGGACCCCCCCTTCCGACCCCCCTTCCGTGCCCCCAACTGTGAATCTGTAAATAAGGCC
CAAGGAACATGTCGGGAGGGGTGAGACACAAAACCGGCCTGCCCTGCAGGATGGGGCTCCACAGGCCGTGCCCAA
CTGGGGTGGTTCTAGGGGAACAGGGGCGGGGAGCTGTTTCTATTTATTATTATTATTATTATTATTATTAT
TGATCAATCTCTGCGGGGTGGGGGTGGGGAGGGAGCTTGGTGGCTTAGCAGATCCGGACAGGCCCT
CTGTCCCTGTGTCGTCCCAACCTCGGTTTCGCGTGATCCTGTCCTGTCCCCCCGACCTTCTGTACGGAT
TTGCTCTCCGAAGGAATTCTGGTTTCGCGTTTCGCGTGTCTCTGATTCCGCCGGCGGCAAAAAAAAA
AAAAAAAAAAAAAAAAAAAAAAGATAATAATAAATAGCCTTGATCAGGGAA
```

FIG. 3A-1

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).

```
HMM file:            /prod/ddm/seqanal/PFAM/pfam5.5/Pfam
Sequence file:       /prod/ddm/wspace/orfanal/oa-script.23506.seq
```

Query: 55053

Scores for sequence family classification (score includes all domains):

| Model | Description | Score | E-value | N |
|---|---|---|---|---|
| pkinase | Protein kinase domain | 323.4 | 2.6e-93 | 1 |
| UBA | UBA domain | 7.7 | 4.9 | 1 |

Parsed for domains:

| Model | Domain | seq-f | seq-t | hmm-f | hmm-t | score | E-value |
|---|---|---|---|---|---|---|---|
| pkinase | 1/1 | 34 | 285 .. | 1 | 278 [] | 323.4 | 2.6e-93 |
| UBA | 1/1 | 315 | 356 .. | 1 | 41 [] | 7.7 | 4.9 |

FIG. 3A-2

```
Alignments of top-scoring domains:
pkinase: domain 1 of 1, from 34 to 285: score 323.4, E = 2.6e-93

*->yelleklGeGsfGkVykakhk.tgkivAvKilkkesls.......lr
                       y+l ++lG+G  G V+++++h  tg++vA+Ki+++e+ls++    + r
          55053   34  YRLEKTLGKGQTGLVKLGVHCiTGQKVAIKIVNREKLSesvlmkvER    80

EiqilkrlshpnivrllgvfedtddhlylvmEymeggGdLfdylrrngpls
                       Ei+ilk + Hp++++l+++v+e   +++lylv+E++ gG+Lfdyl+++g+l+
          55053   81  EIAILKLIEHPHVLKLHDVYE-NKKYLYLVLEHVSGGELFDYLVKKGRLT  129 ekeakkialQilrGleYLHsngivHRDLKpeNILldengtvKiaDFGLAr
                       +kea+k+++Qi+++l+++Hs +i+HRDLKpeN+Llde+++++iaDFG+A
          55053  130  PKEARKFFRQIVSALDFCHSYSICHRDLKPENLLLDEKNNIRIADFGMAS  179 ll...ekltfvGTpwYmmAPEvileg.rgysskvDvWSlGvilyElltg
                       l    +++ l t +G+p+Y   PEv  ++g++++++++D+WS+GviL+ ll g
          55053  180  LQvgdSLLETSCGSPHYA-CPEV-IKGeKYDGRRADMWSCGVILFALLVG  227 gplfpgadlpaftggdevdqliifvlklPfsdelpktridpleelfrikk
                                                     lPf+d   d+l++l++ +k
          55053  228  ---------------------------------ALPFDD-------DNLRQLLEKVK  244 r.rlplpsncSeelkdLlkkcLnkDPskRpGsatakeilnhpwf<-*
                       r+ + p+ +++++++Ll++++++ P+kR+ + ++i +hpw
          55053  245  RgVFHMPHFIPPDCQSLLRGMIEVEPEKRL---SLEQIQKHPWY      285
```

FIG. 3A-3

```
UBA: domain 1 of 1, from 315 to 356: score 7.7, E = 4.9
             *->edeekieqLveMGF..dreevkALratngngverAaewLlsh<-*
                d + +e++ ++G   +dre+ + Lr+  n  e+ ++++Ll +
     55053  315  LDPDVLESMASLGCfrDRERLHRELRSEEEN-QEKMIYYLLLD  356

//
Searching for complete domains in SMART
hmmpfam - search a single seq against HMM database
HMMER 2.1.1 (Dec 1998)
Copyright (C) 1992-1998 Washington University School of Medicine
HMMER is freely distributed under the GNU General Public License (GPL).

- - - - - - - - - - - - - - - - - - - - - - - - - - - - - - - -
HMM file:        /ddm/robison/smart/smart/smart.all.hmms
Sequence file:   /prod/ddm/wspace/orfanal/oa-script.23506.seq
- - - - - - - - - - - - - - - - - - - - - - - - - - - - - - - -
Query:   55053
```

FIG. 3B-1

```
Scores for sequence family classification (score includes all domains):
Model       Description                                      Score    E-value  N
---------   -----------                                      -----    -------  -
serkin_6                                                     356.8    2.4e-103 1
tyrkin_6                                                     39.2     2.4e-14  1

Parsed for domains:
Model       Domain   seq-f   seq-t      hmm-f hmm-t         score    E-value
---------   ------   -----   -----      ----- -----         -----    -------
serkin_6     1/1      34      285  ..      1   231  []     356.8    2.4e-103
tyrkin_6     1/1      34      286  ..      1   280  []      39.2    2.4e-14

Alignments of top-scoring domains:
serkin_6: domain 1 of 1, from 34 to 285: score 356.8, E = 2.4e-103
                   *->YellkklGkGaFGkVylardkktgrlvAikvik......erilr
                      Y+l k+lGkG  G V+l+++  tg++vAiK++++++ +++    +++r
       55053    34   YRLEKTLGKGQTGLVKLGVHCITGQKVAIKIVNreklsesvlMKVER  80

EikiLkk.dHPNIVkLlydvfed.dklylVmEyceGdlGdLfdllkkrgrr
                   Ei+iLk    HP++  kL+ +dv+e++++lylV+E+++G  G+Lfd+l+k+gr
       55053    81  EIAILKLiEHPHVLKLHDVYENKKYLYLVLEHVSG--GELFDYLVKKGR- 127 glrkvlsE.earfyfrQilsaLeYLHsqgIiHRDLKPeNiLLds..hvKl
                   l+++ear++frQi+saL+++Hs  I+HRDLKPeN+LLd+++++  +
       55053   128  -----LTPkEARKFFRQIVSALDFCHSYSICHRDLKPENLLLDEknNIRI 172
```

FIG. 3B-2

```
              aDFGlArql......ttfvGTpeYmAPEvl...gYgkpavDiWSlGcily
              aDFG+A +   +++    t  +G+p+Y   PEv+++++Y++++D+WS+G+il+
55053    173  ADFGMASLQvgdsllETSCGSPHYACPEVIkgeKYDGRRADMWSCGVILF  222

ElltGkpPFp..qldlifkkig........SpeakdLikkLlvkdPek
              ll+G   PF++++l  ++++k+++++  +  ++   +p++  +L++++  +++Pek
55053    223  ALLVGALPFDddNLRQLLEKVKrgvfhmphfiPPDCQSLLRGMIEVEPEK  272

Rlta.ealededldikaHPff<-*
              Rl+   +   +++  +     HP+
55053    273  RLSLeQIQK------HPWY  285
```

```
tyrkin_6: domain 1 of 1, from 34 to 286: score 39.2, E = 2.4e-14
                *->ltlgkkLGeGaFGeVykGtlk...ieVAVKtLkeda.....keeFlr
                   +l+k+LG G+ G  V +G+    +++VA+K ++ ++ +++ ++    r
        55053  34  YRLEKTLGKGQTGLVKLGVHCitgQKVAIKIVNREKlsesvLMKVER 80

EakiMkklGgkHpNiVkLlGvcteegrrFmevePlmivmEymegGdLldy
                   E+ i+k + +Hp+++kL+ v  +        + l++v+E+++gG L dy
        55053  81  EIAILKLI--EHPHVLKLHDVYENK-------KYLYLVLEHVSGGELFDY 121

LrknrpklslsdLlsfAlQIAkGMeYLesknfvHRDLAARNcLvgenkvv
                   L k+++ l++++  +f  QI +  ++ +s  +  HRDL   N L++e++  +
        55053 122  LVKKGR-LTPKEARKFFRQIVSALDFCHSYSICHRDLKPENLLLDEKNNI 170

KIsDFGLsRdlyddDkkGeskdyYrkkggkggktllPirWmAPEslkdgk
                   +I+DFG++        d      +   ++   g+          PE++k   k
        55053 171  RIADFGMASLQVGD-------SLLETSC--GSP-----HYACPEVIKGEK 206

Ft.skSDVWSFGVlLWEiftlGeqPYpgeiqqfmsneevleylkkGyRlp
                   +  +   D WS GV L+ ++   G+ P   +   + +++le++k+G
        55053 207  YDgRRADMWSCGVILFALL-VGALPFDD-----DNLRQLLEKVKRG-VFH 249 kPendlpiSsvtCPdelYdlMlqCWaedPedRPtFsel...verl<-*
                   P+          P++ +l +   + +Pe+R + ++++++  +l
        55053 250  MPHF--------IPPDCQSLLRGMIEVEPEKRLSLEQIqkhPWYL     286
```

Fig. 3C

SEQUENCE LISTING

<160> NUMBER OF SEQ ID NOS: 8

<210> SEQ ID NO 1
<211> LENGTH: 2980
<212> TYPE: DNA
<213> ORGANISM: Homo sapiens
<220> FEATURE:

-continued

```
<221> NAME/KEY: CDS
<222> LOCATION: (86)...(2419)

<400> SEQUENCE: 1
gtcgacccac gcgtccgcgg acgcgtgggc ggacgcgtgg gcggacgcgt ggggggggac         60
cggtcgggcc gggaccaagg gcacc atg tcg tcc ggg gcc aag gag gga ggt         112
                            Met Ser Ser Gly Ala Lys Glu Gly Gly
                              1               5 ggg ggc tct ccc gcc tac cac ctc ccc cac ccc cac ccc cac cca ccc         160
Gly Gly Ser Pro Ala Tyr His Leu Pro His Pro His Pro His Pro Pro
 10              15                  20                  25 cag cac gcc caa tat gtg ggc ccc tat cgg ctg gag aag acg ctg ggc         208
Gln His Ala Gln Tyr Val Gly Pro Tyr Arg Leu Glu Lys Thr Leu Gly
             30                  35                  40 aaa gga cag aca ggg ctg gtt aaa ctc ggg gtc cac tgc atc acg ggt         256
Lys Gly Gln Thr Gly Leu Val Lys Leu Gly Val His Cys Ile Thr Gly
         45                  50                  55 cag aag gtc gcc atc aag atc gtg aac cgg gag aag ctg tcg gag tcg         304
Gln Lys Val Ala Ile Lys Ile Val Asn Arg Glu Lys Leu Ser Glu Ser
     60                  65                  70 gtg ctg atg aag gtg gag cgg gag atc gcc atc ctg aag ctc atc gaa         352
Val Leu Met Lys Val Glu Arg Glu Ile Ala Ile Leu Lys Leu Ile Glu
 75                  80                  85 cac cca cat gtc ctc aag ctc cac gac gtc tac gag aac aag aaa tat         400
His Pro His Val Leu Lys Leu His Asp Val Tyr Glu Asn Lys Lys Tyr
 90                  95                 100                 105 ttg tac ctg gtt ctg gag cac gtc tcg ggg ggt gag cta ttc gac tac         448
Leu Tyr Leu Val Leu Glu His Val Ser Gly Gly Glu Leu Phe Asp Tyr
             110                 115                 120 ctg gta aag aag ggg aga ctg acg ccc aag gag gcc cga aag ttc ttc         496
Leu Val Lys Lys Gly Arg Leu Thr Pro Lys Glu Ala Arg Lys Phe Phe
         125                 130                 135 cgc cag att gtg tct gcg ctg gac ttc tgc cac agc tac tcc atc tgc         544
Arg Gln Ile Val Ser Ala Leu Asp Phe Cys His Ser Tyr Ser Ile Cys
     140                 145                 150 cac aga gac cta aag ccc gag aac ctg ctt ttg gat gag aaa aac aac         592
His Arg Asp Leu Lys Pro Glu Asn Leu Leu Leu Asp Glu Lys Asn Asn
155                 160                 165 atc cgc att gca gac ttc ggc atg gcg tcc ctg cag gtg ggg gac agc         640
Ile Arg Ile Ala Asp Phe Gly Met Ala Ser Leu Gln Val Gly Asp Ser
170                 175                 180                 185 ctc ctg gag acc agc tgc ggg tcc ccc cat tat gcg tgt cca gag gtg         688
Leu Leu Glu Thr Ser Cys Gly Ser Pro His Tyr Ala Cys Pro Glu Val
             190                 195                 200 att aag ggg gaa aaa tat gat ggc cgc cgg gca gac atg tgg agc tgt         736
Ile Lys Gly Glu Lys Tyr Asp Gly Arg Arg Ala Asp Met Trp Ser Cys
         205                 210                 215 gga gtc atc ctc ttc gcc ctg ctc gtg ggg gct ctg ccc ttt gat gac         784
Gly Val Ile Leu Phe Ala Leu Leu Val Gly Ala Leu Pro Phe Asp Asp
     220                 225                 230 gac aac ctc cgc cag ctg ctg gag aag gtg aaa cgg ggc gtc ttc cac         832
Asp Asn Leu Arg Gln Leu Leu Glu Lys Val Lys Arg Gly Val Phe His
235                 240                 245 atg ccc cac ttc att cct cca gat tgc cag agc ctc ctg agg gga atg         880
Met Pro His Phe Ile Pro Pro Asp Cys Gln Ser Leu Leu Arg Gly Met
250                 255                 260                 265 atc gaa gtg gag ccc gaa aaa agg ctc agt ctg gag caa att cag aaa         928
Ile Glu Val Glu Pro Glu Lys Arg Leu Ser Leu Glu Gln Ile Gln Lys
             270                 275                 280
```

-continued

| | | |
|---|---|---|
| cat cct tgg tac cta ggc ggg aaa cac gag cca gac ccg tgc ctg gag<br>His Pro Trp Tyr Leu Gly Gly Lys His Glu Pro Asp Pro Cys Leu Glu<br>285　　　　　　　　290　　　　　　　　295 | | 976 |
| cca gcc cct ggc cgc cgg gta gcc atg cgg agc ctg cca tcc aac gga<br>Pro Ala Pro Gly Arg Arg Val Ala Met Arg Ser Leu Pro Ser Asn Gly<br>300　　　　　　　　305　　　　　　　　310 | | 1024 |
| gag ctg gac ccc gac gtc cta gag agc atg gca tca ctg ggc tgc ttc<br>Glu Leu Asp Pro Asp Val Leu Glu Ser Met Ala Ser Leu Gly Cys Phe<br>315　　　　　　　　320　　　　　　　　325 | | 1072 |
| agg gac cgc gag agg ctg cat cgc gag ctg cgc agt gag gag gag aac<br>Arg Asp Arg Glu Arg Leu His Arg Glu Leu Arg Ser Glu Glu Glu Asn<br>330　　　　　　　　335　　　　　　　　340　　　　　　　　345 | | 1120 |
| caa gaa aag atg ata tat tat ctg ctt ttg gat cgg aag gag cgg tat<br>Gln Glu Lys Met Ile Tyr Tyr Leu Leu Leu Asp Arg Lys Glu Arg Tyr<br>350　　　　　　　　355　　　　　　　　360 | | 1168 |
| ccc agc tgt gag gac cag gac ctg cct ccc cgg aat gat gtt gac ccc<br>Pro Ser Cys Glu Asp Gln Asp Leu Pro Pro Arg Asn Asp Val Asp Pro<br>365　　　　　　　　370　　　　　　　　375 | | 1216 |
| ccc cgg aag cgt gtg gat tct ccc atg ctg agc cgt cac ggg aag cgg<br>Pro Arg Lys Arg Val Asp Ser Pro Met Leu Ser Arg His Gly Lys Arg<br>380　　　　　　　　385　　　　　　　　390 | | 1264 |
| cga cca gag cgg aag tcc atg gaa gtc ctg agc atc acc gat gcc ggg<br>Arg Pro Glu Arg Lys Ser Met Glu Val Leu Ser Ile Thr Asp Ala Gly<br>395　　　　　　　　400　　　　　　　　405 | | 1312 |
| ggt ggt ggc tcc cct gta ccc acc cga cgg gcc ttg gag atg gcc cag<br>Gly Gly Gly Ser Pro Val Pro Thr Arg Arg Ala Leu Glu Met Ala Gln<br>410　　　　　　　　415　　　　　　　　420　　　　　　　　425 | | 1360 |
| cac agc cag aga tcc cgt agc gtc agt gga gcc tcc acg ggt ctg tcc<br>His Ser Gln Arg Ser Arg Ser Val Ser Gly Ala Ser Thr Gly Leu Ser<br>430　　　　　　　　435　　　　　　　　440 | | 1408 |
| tcc agc cct cta agc agc cca agg agt ccg gtc ttt tcc ttt tca ccg<br>Ser Ser Pro Leu Ser Ser Pro Arg Ser Pro Val Phe Ser Phe Ser Pro<br>445　　　　　　　　450　　　　　　　　455 | | 1456 |
| gag ccg ggg gct gga gat gag gct cga ggc ggg ggc tcc ccg act tcc<br>Glu Pro Gly Ala Gly Asp Glu Ala Arg Gly Gly Gly Ser Pro Thr Ser<br>460　　　　　　　　465　　　　　　　　470 | | 1504 |
| aaa acg cag acg ctg cct tct cgg ggc ccc agg ggt ggg ggc gcc ggg<br>Lys Thr Gln Thr Leu Pro Ser Arg Gly Pro Arg Gly Gly Gly Ala Gly<br>475　　　　　　　　480　　　　　　　　485 | | 1552 |
| gag cag ccc ccg ccc ccc agt gcc cgc tcc aca ccc ctg ccc ggc ccc<br>Glu Gln Pro Pro Pro Pro Ser Ala Arg Ser Thr Pro Leu Pro Gly Pro<br>490　　　　　　　　495　　　　　　　　500　　　　　　　　505 | | 1600 |
| cca ggc tcc ccg cgc tcc tct ggc ggg acc ccc ttg cac tcg cct ctg<br>Pro Gly Ser Pro Arg Ser Ser Gly Gly Thr Pro Leu His Ser Pro Leu<br>510　　　　　　　　515　　　　　　　　520 | | 1648 |
| cac acg ccc cgg gcc agt ccc acc ggg acc ccg ggg aca aca cca ccc<br>His Thr Pro Arg Ala Ser Pro Thr Gly Thr Pro Gly Thr Thr Pro Pro<br>525　　　　　　　　530　　　　　　　　535 | | 1696 |
| ccc agc ccc ggt ggt ggc gtc ggg gga gcc gcc tgg agg agt cgt ctc<br>Pro Ser Pro Gly Gly Gly Val Gly Gly Ala Ala Trp Arg Ser Arg Leu<br>540　　　　　　　　545　　　　　　　　550 | | 1744 |
| aac tcc atc cgc aac agc ttc ctg ggc tcc cct cgc ttt cac cgg cgc<br>Asn Ser Ile Arg Asn Ser Phe Leu Gly Ser Pro Arg Phe His Arg Arg<br>555　　　　　　　　560　　　　　　　　565 | | 1792 |
| aag atg cag gtc cct acc gct gag gag atg tcc agc ttg acg cca gag<br>Lys Met Gln Val Pro Thr Ala Glu Glu Met Ser Ser Leu Thr Pro Glu<br>570　　　　　　　　575　　　　　　　　580　　　　　　　　585 | | 1840 |
| tcc tcc ccg gag ctg gca aaa cgc tcc tgg ttc ggg aac ttc atc tcc<br>Ser Ser Pro Glu Leu Ala Lys Arg Ser Trp Phe Gly Asn Phe Ile Ser<br>590　　　　　　　　595　　　　　　　　600 | | 1888 |

```
ttg gac aaa gaa gaa caa ata ttc ctc gtg cta aag gac aaa cct ctc      1936
Leu Asp Lys Glu Glu Gln Ile Phe Leu Val Leu Lys Asp Lys Pro Leu
        605                 610                 615 agc agc atc aaa gca gac atc gtc cat gcc ttt ctg tcg atc ccc agc      1984
Ser Ser Ile Lys Ala Asp Ile Val His Ala Phe Leu Ser Ile Pro Ser
            620                 625                 630 ctg agt cac agt gtg ctg tca cag acc agc ttc agg gcc gag tac aag      2032
Leu Ser His Ser Val Leu Ser Gln Thr Ser Phe Arg Ala Glu Tyr Lys
        635                 640                 645 gcc agt ggc ggc ccc tcc gtc ttc caa aag ccc gtc cgc ttc cag gtg      2080
Ala Ser Gly Gly Pro Ser Val Phe Gln Lys Pro Val Arg Phe Gln Val
650                 655                 660                 665 gac atc agc tcc tct gag ggt cca gag ccc tcc ccg cga cgg gac ggc      2128
Asp Ile Ser Ser Ser Glu Gly Pro Glu Pro Ser Pro Arg Arg Asp Gly
            670                 675                 680 agc gga ggt ggt ggc atc tac tcc gtc acc ttc act ctc atc tcg ggt      2176
Ser Gly Gly Gly Gly Ile Tyr Ser Val Thr Phe Thr Leu Ile Ser Gly
        685                 690                 695 ccc agc cgt cgg ttc aag cga gtg gtg gag acc atc cag gca cag ctc      2224
Pro Ser Arg Arg Phe Lys Arg Val Val Glu Thr Ile Gln Ala Gln Leu
700                 705                 710 ctg agc act cat gac cag ccc tcc gtg cag gcc ctg gca gac gag aag      2272
Leu Ser Thr His Asp Gln Pro Ser Val Gln Ala Leu Ala Asp Glu Lys
    715                 720                 725 aac ggg gcc cag acc cgg cct gct ggt gcc cca ccc cga agc ctg cag      2320
Asn Gly Ala Gln Thr Arg Pro Ala Gly Ala Pro Pro Arg Ser Leu Gln
730                 735                 740                 745 ccc cca ccc ggc cgc cca gac cca gag ctg agc agc tct ccc cgc cga      2368
Pro Pro Pro Gly Arg Pro Asp Pro Glu Leu Ser Ser Ser Pro Arg Arg
            750                 755                 760 ggc ccc ccc aag gac aag aag ctc ctg gcc acc aac ggg acc cct ctg      2416
Gly Pro Pro Lys Asp Lys Lys Leu Leu Ala Thr Asn Gly Thr Pro Leu
        765                 770                 775 ccc tgaccccacg gggccgggga gggaggggac cccctccac ccccttccg             2469
Pro tgccccccaa ctgtgaatct gtaaataagg cccaaggaac atgtcgggag ggggtggac     2529 acaaaaaccg gccttgccct gcagggatgg ggctccacag gccgtgccca actgggggtg   2589
gttctagggg aacagggggc gggggagctg tttctatttt atttattgat taatttatta   2649
ttttatttat tgatcaatct ctctgcgggg tggggtgggg gagggacggg agctggttgg   2709
ggtggcttag cagatccgga cagggccctc tgtccctgtg tcgtcccaa ccccctcttc    2769 ccgggcccct cctcccctgg tcctccccc acgaccttct gtacggattt gctctccgga    2829
aggaattctg gtttcgcgtg atcctgcctg cgtccgtgtc tctgattccg ccggcggcaa   2889 aaaaaaaaa aaaaaaaaa aaaaaaaag ataataataa taaatagcct tgatcaggga     2949
aaaaaaaaaa aaaaaaaaag ggcggccgct a                                   2980

<210> SEQ ID NO 2
<211> LENGTH: 778
<212> TYPE: PRT
<213> ORGANISM: Homo sapiens

<400> SEQUENCE: 2

Met Ser Ser Gly Ala Lys Glu Gly Gly Gly Ser Pro Ala Tyr His
1               5                   10                  15

Leu Pro His Pro His Pro His Pro Pro Gln His Ala Gln Tyr Val Gly
                20                  25                  30
```

-continued

```
Pro Tyr Arg Leu Glu Lys Thr Leu Gly Lys Gly Gln Thr Gly Leu Val
         35                  40                  45

Lys Leu Gly Val His Cys Ile Thr Gly Gln Lys Val Ala Ile Lys Ile
 50                  55                  60

Val Asn Arg Glu Lys Leu Ser Glu Ser Val Leu Met Lys Val Glu Arg
 65                  70                  75                  80

Glu Ile Ala Ile Leu Lys Leu Ile Glu His Pro His Val Leu Lys Leu
                 85                  90                  95

His Asp Val Tyr Glu Asn Lys Lys Tyr Leu Tyr Leu Val Leu Glu His
            100                 105                 110

Val Ser Gly Gly Glu Leu Phe Asp Tyr Leu Val Lys Lys Gly Arg Leu
            115                 120                 125

Thr Pro Lys Glu Ala Arg Lys Phe Phe Arg Gln Ile Val Ser Ala Leu
            130                 135                 140

Asp Phe Cys His Ser Tyr Ser Ile Cys His Arg Asp Leu Lys Pro Glu
145                 150                 155                 160

Asn Leu Leu Leu Asp Glu Lys Asn Asn Ile Arg Ile Ala Asp Phe Gly
                165                 170                 175

Met Ala Ser Leu Gln Val Gly Asp Ser Leu Leu Glu Thr Ser Cys Gly
            180                 185                 190

Ser Pro His Tyr Ala Cys Pro Glu Val Ile Lys Gly Glu Lys Tyr Asp
            195                 200                 205

Gly Arg Arg Ala Asp Met Trp Ser Cys Gly Val Ile Leu Phe Ala Leu
            210                 215                 220

Leu Val Gly Ala Leu Pro Phe Asp Asp Asp Asn Leu Arg Gln Leu Leu
225                 230                 235                 240

Glu Lys Val Lys Arg Gly Val Phe His Met Pro His Phe Ile Pro Pro
                245                 250                 255

Asp Cys Gln Ser Leu Leu Arg Gly Met Ile Glu Val Glu Pro Glu Lys
            260                 265                 270

Arg Leu Ser Leu Glu Gln Ile Gln Lys His Pro Trp Tyr Leu Gly Gly
            275                 280                 285

Lys His Glu Pro Asp Pro Cys Leu Glu Pro Ala Pro Gly Arg Arg Val
            290                 295                 300

Ala Met Arg Ser Leu Pro Ser Asn Gly Glu Leu Asp Pro Asp Val Leu
305                 310                 315                 320

Glu Ser Met Ala Ser Leu Gly Cys Phe Arg Asp Arg Glu Arg Leu His
                325                 330                 335

Arg Glu Leu Arg Ser Glu Glu Asn Gln Glu Lys Met Ile Tyr Tyr
            340                 345                 350

Leu Leu Leu Asp Arg Lys Glu Arg Tyr Pro Ser Cys Glu Asp Gln Asp
            355                 360                 365

Leu Pro Pro Arg Asn Asp Val Asp Pro Pro Arg Lys Arg Val Asp Ser
            370                 375                 380

Pro Met Leu Ser Arg His Gly Lys Arg Pro Glu Arg Lys Ser Met
385                 390                 395                 400

Glu Val Leu Ser Ile Thr Asp Ala Gly Gly Gly Ser Pro Val Pro
                405                 410                 415

Thr Arg Arg Ala Leu Glu Met Ala Gln His Ser Gln Arg Ser Arg Ser
            420                 425                 430

Val Ser Gly Ala Ser Thr Gly Leu Ser Ser Ser Pro Leu Ser Ser Pro
            435                 440                 445
```

```
Arg Ser Pro Val Phe Ser Phe Ser Pro Glu Pro Gly Ala Gly Asp Glu
    450                 455                 460

Ala Arg Gly Gly Gly Ser Pro Thr Ser Lys Thr Gln Thr Leu Pro Ser
465                 470                 475                 480

Arg Gly Pro Arg Gly Gly Ala Gly Glu Gln Pro Pro Pro Ser
                485                 490                 495

Ala Arg Ser Thr Pro Leu Pro Gly Pro Pro Gly Ser Pro Arg Ser Ser
                500                 505                 510

Gly Gly Thr Pro Leu His Ser Pro Leu His Thr Pro Arg Ala Ser Pro
            515                 520                 525

Thr Gly Thr Pro Gly Thr Thr Pro Pro Ser Pro Gly Gly Val
    530                 535                 540

Gly Gly Ala Ala Trp Arg Ser Arg Leu Asn Ser Ile Arg Asn Ser Phe
545                 550                 555                 560

Leu Gly Ser Pro Arg Phe His Arg Arg Lys Met Gln Val Pro Thr Ala
                565                 570                 575

Glu Glu Met Ser Ser Leu Thr Pro Glu Ser Ser Pro Glu Leu Ala Lys
                580                 585                 590

Arg Ser Trp Phe Gly Asn Phe Ile Ser Leu Asp Lys Glu Glu Gln Ile
            595                 600                 605

Phe Leu Val Leu Lys Asp Lys Pro Leu Ser Ser Ile Lys Ala Asp Ile
610                 615                 620

Val His Ala Phe Leu Ser Ile Pro Ser Leu Ser His Ser Val Leu Ser
625                 630                 635                 640

Gln Thr Ser Phe Arg Ala Glu Tyr Lys Ala Ser Gly Gly Pro Ser Val
                645                 650                 655

Phe Gln Lys Pro Val Arg Phe Gln Val Asp Ile Ser Ser Ser Glu Gly
                660                 665                 670

Pro Glu Pro Ser Pro Arg Arg Asp Gly Ser Gly Gly Gly Ile Tyr
            675                 680                 685

Ser Val Thr Phe Thr Leu Ile Ser Gly Pro Ser Arg Arg Phe Lys Arg
    690                 695                 700

Val Val Glu Thr Ile Gln Ala Gln Leu Leu Ser Thr His Asp Gln Pro
705                 710                 715                 720

Ser Val Gln Ala Leu Ala Asp Glu Lys Asn Gly Ala Gln Thr Arg Pro
                725                 730                 735

Ala Gly Ala Pro Pro Arg Ser Leu Gln Pro Pro Gly Arg Pro Asp
            740                 745                 750

Pro Glu Leu Ser Ser Ser Pro Arg Arg Gly Pro Pro Lys Asp Lys Lys
    755                 760                 765

Leu Leu Ala Thr Asn Gly Thr Pro Leu Pro
    770                 775

<210> SEQ ID NO 3
<211> LENGTH: 2334
<212> TYPE: DNA
<213> ORGANISM: Homo sapiens
<220> FEATURE:
<221> NAME/KEY: CDS
<222> LOCATION: (1)...(2334)

<400> SEQUENCE: 3 atg tcg tcc ggg gcc aag gag gga ggt ggg ggc tct ccc gcc tac cac    48
Met Ser Ser Gly Ala Lys Glu Gly Gly Gly Gly Ser Pro Ala Tyr His
 1               5                  10                  15 ctc ccc cac ccc cac ccc cac cca ccc cag cac gcc caa tat gtg ggc    96
```

-continued

| | | | | | | | | | | | | | | | | |
|---|---|---|---|---|---|---|---|---|---|---|---|---|---|---|---|---|
| Leu | Pro | His | Pro | His | Pro | His | Pro | Pro | Gln | His | Ala | Gln | Tyr | Val | Gly | |
| | | 20 | | | | 25 | | | | 30 | | | | | | |

```
ccc tat cgg ctg gag aag acg ctg ggc aaa gga cag aca ggg ctg gtt       144
Pro Tyr Arg Leu Glu Lys Thr Leu Gly Lys Gly Gln Thr Gly Leu Val
         35                  40                  45 aaa ctc ggg gtc cac tgc atc acg ggt cag aag gtc gcc atc aag atc       192
Lys Leu Gly Val His Cys Ile Thr Gly Gln Lys Val Ala Ile Lys Ile
 50                  55                  60 gtg aac cgg gag aag ctg tcg gag tcg gtg ctg atg aag gtg gag cgg       240
Val Asn Arg Glu Lys Leu Ser Glu Ser Val Leu Met Lys Val Glu Arg
 65                  70                  75                  80 gag atc gcc atc ctg aag ctc atc gaa cac cca cat gtc ctc aag ctc       288
Glu Ile Ala Ile Leu Lys Leu Ile Glu His Pro His Val Leu Lys Leu
                 85                  90                  95 cac gac gtc tac gag aac aag aaa tat ttg tac ctg gtt ctg gag cac       336
His Asp Val Tyr Glu Asn Lys Lys Tyr Leu Tyr Leu Val Leu Glu His
                100                 105                 110 gtc tcg ggg ggt gag cta ttc gac tac ctg gta aag aag ggg aga ctg       384
Val Ser Gly Gly Glu Leu Phe Asp Tyr Leu Val Lys Lys Gly Arg Leu
            115                 120                 125 acg ccc aag gag gcc cga aag ttc ttc cgc cag att gtg tct gcg ctg       432
Thr Pro Lys Glu Ala Arg Lys Phe Phe Arg Gln Ile Val Ser Ala Leu
        130                 135                 140 gac ttc tgc cac agc tac tcc atc tgc cac aga gac cta aag ccc gag       480
Asp Phe Cys His Ser Tyr Ser Ile Cys His Arg Asp Leu Lys Pro Glu
145                 150                 155                 160 aac ctg ctt ttg gat gag aaa aac aac atc cgc att gca gac ttc ggc       528
Asn Leu Leu Leu Asp Glu Lys Asn Asn Ile Arg Ile Ala Asp Phe Gly
                165                 170                 175 atg gcg tcc ctg cag gtg ggg gac agc ctc ctg gag acc agc tgc ggg       576
Met Ala Ser Leu Gln Val Gly Asp Ser Leu Leu Glu Thr Ser Cys Gly
            180                 185                 190 tcc ccc cat tat gcg tgt cca gag gtg att aag ggg gaa aaa tat gat       624
Ser Pro His Tyr Ala Cys Pro Glu Val Ile Lys Gly Glu Lys Tyr Asp
        195                 200                 205 ggc cgc cgg gca gac atg tgg agc tgt gga gtc atc ctc ttc gcc ctg       672
Gly Arg Arg Ala Asp Met Trp Ser Cys Gly Val Ile Leu Phe Ala Leu
210                 215                 220 ctc gtg ggg gct ctg ccc ttt gat gac gac aac ctc cgc cag ctg ctg       720
Leu Val Gly Ala Leu Pro Phe Asp Asp Asp Asn Leu Arg Gln Leu Leu
225                 230                 235                 240 gag aag gtg aaa cgg ggc gtc ttc cac atg ccc cac ttc att cct cca       768
Glu Lys Val Lys Arg Gly Val Phe His Met Pro His Phe Ile Pro Pro
                245                 250                 255 gat tgc cag agc ctc ctg agg gga atg atc gaa gtg gag ccc gaa aaa       816
Asp Cys Gln Ser Leu Leu Arg Gly Met Ile Glu Val Glu Pro Glu Lys
            260                 265                 270 agg ctc agt ctg gag caa att cag aaa cat cct tgg tac cta ggc ggg       864
Arg Leu Ser Leu Glu Gln Ile Gln Lys His Pro Trp Tyr Leu Gly Gly
        275                 280                 285 aaa cac gag cca gac ccg tgc ctg gag cca gcc cct ggc cgc cgg gta       912
Lys His Glu Pro Asp Pro Cys Leu Glu Pro Ala Pro Gly Arg Arg Val
    290                 295                 300 gcc atg cgg agc ctg cca tcc aac gga gag ctg gac ccc gac gtc cta       960
Ala Met Arg Ser Leu Pro Ser Asn Gly Glu Leu Asp Pro Asp Val Leu
305                 310                 315                 320 gag agc atg gca tca ctg ggc tgc ttc agg gac cgc gag agg ctg cat      1008
Glu Ser Met Ala Ser Leu Gly Cys Phe Arg Asp Arg Glu Arg Leu His
                325                 330                 335
```

```
cgc gag ctg cgc agt gag gag gag aac caa gaa aag atg ata tat tat       1056
Arg Glu Leu Arg Ser Glu Glu Glu Asn Gln Glu Lys Met Ile Tyr Tyr
        340                 345                 350 ctg ctt ttg gat cgg aag gag cgg tat ccc agc tgt gag gac cag gac       1104
Leu Leu Leu Asp Arg Lys Glu Arg Tyr Pro Ser Cys Glu Asp Gln Asp
355                 360                 365 ctg cct ccc cgg aat gat gtt gac ccc ccc cgg aag cgt gtg gat tct       1152
Leu Pro Pro Arg Asn Asp Val Asp Pro Pro Arg Lys Arg Val Asp Ser
    370                 375                 380 ccc atg ctg agc cgt cac ggg aag cgg cga cca gag cgg aag tcc atg       1200
Pro Met Leu Ser Arg His Gly Lys Arg Arg Pro Glu Arg Lys Ser Met
385                 390                 395                 400 gaa gtc ctg agc atc acc gat gcc ggg ggt ggt ggc tcc cct gta ccc       1248
Glu Val Leu Ser Ile Thr Asp Ala Gly Gly Gly Gly Ser Pro Val Pro
                405                 410                 415 acc cga cgg gcc ttg gag atg gcc cag cac agc cag aga tcc cgt agc       1296
Thr Arg Arg Ala Leu Glu Met Ala Gln His Ser Gln Arg Ser Arg Ser
        420                 425                 430 gtc agt gga gcc tcc acg ggt ctg tcc tcc agc cct cta agc agc cca       1344
Val Ser Gly Ala Ser Thr Gly Leu Ser Ser Ser Pro Leu Ser Ser Pro
435                 440                 445 agg agt ccg gtc ttt tcc ttt tca ccg gag ccg ggg gct gga gat gag       1392
Arg Ser Pro Val Phe Ser Phe Ser Pro Glu Pro Gly Ala Gly Asp Glu
    450                 455                 460 gct cga ggc ggg ggc tcc ccg act tcc aaa acg cag acg ctg cct tct       1440
Ala Arg Gly Gly Gly Ser Pro Thr Ser Lys Thr Gln Thr Leu Pro Ser
465                 470                 475                 480 cgg ggc ccc agg ggt ggg ggc gcc ggg gag cag ccc ccg ccc ccc agt       1488
Arg Gly Pro Arg Gly Gly Gly Ala Gly Glu Gln Pro Pro Pro Pro Ser
                485                 490                 495 gcc cgc tcc aca ccc ctg ccc ggc ccc cca ggc tcc ccg cgc tcc tct       1536
Ala Arg Ser Thr Pro Leu Pro Gly Pro Pro Gly Ser Pro Arg Ser Ser
        500                 505                 510 ggc ggg acc ccc ttg cac tcg cct ctg cac acg ccc cgg gcc agt ccc       1584
Gly Gly Thr Pro Leu His Ser Pro Leu His Thr Pro Arg Ala Ser Pro
515                 520                 525 acc ggg acc ccg ggg aca aca cca ccc ccc agc ccc ggc ggt ggc gtc       1632
Thr Gly Thr Pro Gly Thr Thr Pro Pro Pro Ser Pro Gly Gly Gly Val
    530                 535                 540 ggg gga gcc gcc tgg agg agt cgt ctc aac tcc atc cgc aac agc ttc       1680
Gly Gly Ala Ala Trp Arg Ser Arg Leu Asn Ser Ile Arg Asn Ser Phe
545                 550                 555                 560 ctg ggc tcc cct cgc ttt cac cgg cgc aag atg cag gtc cct acc gct       1728
Leu Gly Ser Pro Arg Phe His Arg Arg Lys Met Gln Val Pro Thr Ala
                565                 570                 575 gag gag atg tcc agc ttg acg cca gag tcc tcc ccg gag ctg gca aaa       1776
Glu Glu Met Ser Ser Leu Thr Pro Glu Ser Ser Pro Glu Leu Ala Lys
        580                 585                 590 cgc tcc tgg ttc ggg aac ttc atc tcc ttg gac aaa gaa gaa caa ata       1824
Arg Ser Trp Phe Gly Asn Phe Ile Ser Leu Asp Lys Glu Glu Gln Ile
595                 600                 605 ttc ctc gtg cta aag gac aaa cct ctc agc agc atc aaa gca gac atc       1872
Phe Leu Val Leu Lys Asp Lys Pro Leu Ser Ser Ile Lys Ala Asp Ile
    610                 615                 620 gtc cat gcc ttt ctg tcg atc ccc agc ctg agt cac agt gtg ctg tca       1920
Val His Ala Phe Leu Ser Ile Pro Ser Leu Ser His Ser Val Leu Ser
625                 630                 635                 640 cag acc agc ttc agg gcc gag tac aag gcc agt ggc ggc ccc tcc gtc       1968
Gln Thr Ser Phe Arg Ala Glu Tyr Lys Ala Ser Gly Gly Pro Ser Val
                645                 650                 655
```

```
ttc caa aag ccc gtc cgc ttc cag gtg gac atc agc tcc tct gag ggt    2016
Phe Gln Lys Pro Val Arg Phe Gln Val Asp Ile Ser Ser Ser Glu Gly
        660                 665                 670 cca gag ccc tcc ccg cga cgg gac ggc agc gga ggt ggt ggc atc tac    2064
Pro Glu Pro Ser Pro Arg Arg Asp Gly Ser Gly Gly Gly Gly Ile Tyr
            675                 680                 685 tcc gtc acc ttc act ctc atc tcg ggt ccc agc cgt cgg ttc aag cga    2112
Ser Val Thr Phe Thr Leu Ile Ser Gly Pro Ser Arg Arg Phe Lys Arg
    690                 695                 700 gtg gtg gag acc atc cag gca cag ctc ctg agc act cat gac cag ccc    2160
Val Val Glu Thr Ile Gln Ala Gln Leu Leu Ser Thr His Asp Gln Pro
705                 710                 715                 720 tcc gtg cag gcc ctg gca gac gag aag aac ggg gcc cag acc cgg cct    2208
Ser Val Gln Ala Leu Ala Asp Glu Lys Asn Gly Ala Gln Thr Arg Pro
                725                 730                 735 gct ggt gcc cca ccc cga agc ctg cag ccc cca ccc ggc cgc cca gac    2256
Ala Gly Ala Pro Pro Arg Ser Leu Gln Pro Pro Pro Gly Arg Pro Asp
            740                 745                 750 cca gag ctg agc agc tct ccc cgc cga ggc ccc ccc aag gac aag aag    2304
Pro Glu Leu Ser Ser Ser Pro Arg Arg Gly Pro Pro Lys Asp Lys Lys
    755                 760                 765 ctc ctg gcc acc aac ggg acc cct ctg ccc                            2334
Leu Leu Ala Thr Asn Gly Thr Pro Leu Pro
    770                 775

<210> SEQ ID NO 4
<211> LENGTH: 13
<212> TYPE: PRT
<213> ORGANISM: Artificial Sequence
<220> FEATURE:
<223> OTHER INFORMATION: serine/threonine kinase signature motif
      consensus sequence
<221> NAME/KEY: VARIANT
<222> LOCATION: 1
<223> OTHER INFORMATION: Xaa= Leu, Ile, Val, Met, Phe, Tyr, or Cys
<221> NAME/KEY: VARIANT
<222> LOCATION: 2, 4, 8, 9
<223> OTHER INFORMATION: Xaa=any amino acids
<221> NAME/KEY: VARIANT
<222> LOCATION: 3
<223> OTHER INFORMATION: Xaa= His or Tyr
<221> NAME/KEY: VARIANT
<222> LOCATION: 6
<223> OTHER INFORMATION: Xaa= Leu, Ile, Val, Met, Phe, or Tyr
<221> NAME/KEY: VARIANT
<222> LOCATION: 11, 12, 13
<223> OTHER INFORMATION: Xaa= Leu, Ile, Val, Met, Phe, Tyr, Cys, or Thr

<400> SEQUENCE: 4

Xaa Xaa Xaa Xaa Asp Xaa Lys Xaa Xaa Asn Xaa Xaa Xaa
 1               5                  10

<210> SEQ ID NO 5
<211> LENGTH: 278
<212> TYPE: PRT
<213> ORGANISM: Artificial Sequence
<220> FEATURE:
<223> OTHER INFORMATION: Eukaryotic protein kinase domain

<400> SEQUENCE: 5

Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
             20                  25                  30

Lys Glu Ser Leu Ser Leu Arg Glu Ile Gln Ile Leu Lys Arg Leu Ser
```

```
                35                  40                  45
His Pro Asn Ile Val Arg Leu Leu Gly Val Phe Glu Asp Thr Asp Asp
         50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                 85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Lys Lys Cys Leu
                245                 250                 255

Asn Lys Asp Pro Ser Lys Arg Pro Gly Ser Ala Thr Ala Lys Glu Ile
            260                 265                 270

Leu Asn His Pro Trp Phe
        275

<210> SEQ ID NO 6
<211> LENGTH: 41
<212> TYPE: PRT
<213> ORGANISM: Artificial Sequence
<220> FEATURE:
<223> OTHER INFORMATION: UBA domain

<400> SEQUENCE: 6

Glu Asp Glu Glu Lys Ile Glu Gln Leu Val Glu Met Gly Phe Asp Arg
 1               5                  10                  15

Glu Glu Val Val Lys Ala Leu Arg Ala Thr Asn Gly Asn Gly Val Glu
            20                  25                  30

Arg Ala Ala Glu Trp Leu Leu Ser His
        35                  40

<210> SEQ ID NO 7
<211> LENGTH: 231
<212> TYPE: PRT
<213> ORGANISM: Artificial Sequence
<220> FEATURE:
<223> OTHER INFORMATION: serkin_6 domain

<400> SEQUENCE: 7

Tyr Glu Leu Leu Lys Lys Leu Gly Lys Gly Ala Phe Gly Lys Val Tyr
 1               5                  10                  15
```

```
Leu Ala Arg Asp Lys Lys Thr Gly Arg Leu Val Ala Ile Lys Val Ile
                20                  25                  30

Lys Glu Arg Ile Leu Arg Glu Ile Lys Ile Leu Lys Lys Asp His Pro
             35                  40                  45

Asn Ile Val Lys Leu Tyr Asp Val Phe Glu Asp Lys Leu Tyr Leu
 50                  55                  60

Val Met Glu Tyr Cys Glu Gly Asp Leu Gly Asp Leu Phe Asp Leu Leu
 65                  70                  75                  80

Lys Lys Arg Gly Arg Arg Gly Leu Arg Lys Val Leu Ser Glu Glu Ala
                 85                  90                  95

Arg Phe Tyr Phe Arg Gln Ile Leu Ser Ala Leu Glu Tyr Leu His Ser
                100                 105                 110

Gln Gly Ile Ile His Arg Asp Leu Lys Pro Glu Asn Ile Leu Leu Asp
                115                 120                 125

Ser His Val Lys Leu Ala Asp Phe Gly Leu Ala Arg Gln Leu Thr Thr
130                 135                 140

Phe Val Gly Thr Pro Glu Tyr Met Ala Pro Glu Val Leu Gly Tyr Gly
145                 150                 155                 160

Lys Pro Ala Val Asp Ile Trp Ser Leu Gly Cys Ile Leu Tyr Glu Leu
                165                 170                 175

Leu Thr Gly Lys Pro Pro Phe Pro Gln Leu Asp Leu Ile Phe Lys Lys
                180                 185                 190

Ile Gly Ser Pro Glu Ala Lys Asp Leu Ile Lys Lys Leu Leu Val Lys
                195                 200                 205

Asp Pro Glu Lys Arg Leu Thr Ala Glu Ala Leu Glu Asp Glu Leu Asp
 210                 215                 220

Ile Lys Ala His Pro Phe Phe
225                 230

<210> SEQ ID NO 8
<211> LENGTH: 280
<212> TYPE: PRT
<213> ORGANISM: Artificial Sequence
<220> FEATURE:
<223> OTHER INFORMATION: tyrkin_6 domain

<400> SEQUENCE: 8

Leu Thr Leu Gly Lys Lys Leu Gly Glu Gly Ala Phe Gly Glu Val Tyr
 1               5                  10                  15

Lys Gly Thr Leu Lys Ile Glu Val Ala Val Lys Thr Leu Lys Glu Asp
                20                  25                  30

Ala Lys Glu Glu Phe Leu Arg Glu Ala Lys Ile Met Lys Lys Leu Gly
                35                  40                  45

Gly Lys His Pro Asn Ile Val Lys Leu Leu Gly Val Cys Thr Glu Glu
 50                  55                  60

Gly Arg Arg Phe Met Glu Val Glu Pro Leu Met Ile Val Met Glu Tyr
 65                  70                  75                  80

Met Glu Gly Gly Asp Leu Leu Asp Tyr Leu Arg Lys Asn Arg Pro Lys
                 85                  90                  95

Leu Ser Leu Ser Asp Leu Leu Ser Phe Ala Leu Gln Ile Ala Lys Gly
                100                 105                 110

Met Glu Tyr Leu Glu Ser Lys Asn Phe Val His Arg Asp Leu Ala Ala
                115                 120                 125

Arg Asn Cys Leu Val Gly Glu Asn Lys Val Val Lys Ile Ser Asp Phe
130                 135                 140
```

-continued

```
Gly Leu Ser Arg Asp Leu Tyr Asp Asp Lys Lys Gly Glu Ser Lys
145                 150                 155                 160

Asp Tyr Tyr Arg Lys Lys Gly Gly Lys Gly Gly Lys Thr Leu Leu Pro
                165             170                     175

Ile Arg Trp Met Ala Pro Glu Ser Leu Lys Asp Gly Lys Phe Thr Ser
            180                 185                 190

Lys Ser Asp Val Trp Ser Phe Gly Val Leu Leu Trp Glu Ile Phe Thr
        195                 200                 205

Leu Gly Glu Gln Pro Tyr Pro Gly Glu Ile Gln Gln Phe Met Ser Asn
    210                 215                 220

Glu Glu Val Leu Glu Tyr Leu Lys Lys Gly Tyr Arg Leu Pro Lys Pro
225                 230                 235                 240

Glu Asn Asp Leu Pro Ile Ser Ser Val Thr Cys Pro Asp Glu Leu Tyr
            245                 250                 255

Asp Leu Met Leu Gln Cys Trp Ala Glu Asp Pro Glu Asp Arg Pro Thr
            260                 265                 270

Phe Ser Glu Leu Val Glu Arg Leu
            275             280
```

55053, A NOVEL HUMAN EUKARYOTIC KINASE AND USES THEREFOR

RELATED APPLICATIONS

This application claims the benefit of U.S. Provisional Application Serial No. 60/248,893, filed Nov. 15, 2000, the entire contents of which are incorporated herein by this reference.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases and phosphatases play critical roles in the regulation of biochemical and morphological changes associated with cellular growth and division (D'Urso, G. et al. (1990) *Science* 250:786–791; Birchmeier, C. et al. (1993) *Bioessays* 15:185–189). They serve as growth factor receptors and signal transducers and have been implicated in cellular transformation and malignancy (Hunter, T. et al. (1992) *Cell* 70:375–387; Posada, J. et al. (1992) *Mol. Biol. Cell* 3:583–592; Hunter, T. et al. (1994) *Cell* 79:573–582). For example, protein kinases have been shown to participate in the transmission of signals from growth-factor receptors (Sturgill, T. W. et al. (1988) *Nature* 344:715–718; Gomez, N. et al. (1991) *Nature* 353:170–173), control of entry of cells into mitosis (Nurse, P. (1990) *Nature* 344:503–508; Maller, J. L. (1991) *Curr. Opin. Cell Biol.* 3:269–275) and regulation of actin bundling (Husain-Chishti, A. et al. (1988) *Nature* 334:718–721).

Protein kinases and phosphatases can be divided into different groups based on either amino acid sequence similarity or specificity for either serine/threonine or tyrosine residues. A small number of dual-specificity kinases and phosphatases have also been described. Within the broad classification, kinases and phosphatases can be further subdivided into families whose members share a higher degree of catalytic domain amino acid sequence identity and also have similar biochemical properties. Most protein kinase and phosphatase family members also share structural features outside the kinase and phosphatase domain, respectively, that reflect their particular cellular roles. These include regulatory domains that control kinase or phosphatase activity or interaction with other proteins (Hanks, S. K. et al. (1988) *Science* 241:42–52). Given the importance of protein kinases in regulating a variety of key cellular processes, in particular, cellular signaling processes, there exists a need for the identification of novel protein kinases as well as therapeutic and diagnostic methods featuring said kinases as well as modulators thereof.

SUMMARY OF THE INVENTION

The present invention is based, at least in part, on the discovery of novel nucleic acid molecules and polypeptides encoded by such nucleic acid molecules, referred to herein "Eukaryotic Protein Kinase-55053" or EPK-55053. The EPK-55053 nucleic acid and polypeptide molecules of the present invention are useful as modulating agents in regulating a variety of cellular processes. Accordingly, in one aspect, this invention provides isolated nucleic acid molecules encoding EPK-55053 polypeptides, as well as nucleic acid fragments suitable as primers or hybridization probes for the detection of protein kinase-encoding nucleic acids.

In one embodiment, the invention features an isolated nucleic acid molecule that includes the nucleotide sequence set forth in SEQ ID NO:1 or SEQ ID NO:3. In another embodiment, the invention features an isolated nucleic acid molecule that encodes a polypeptide including the amino acid sequence set forth in SEQ ID NO:2.

In still other embodiments, the invention features isolated nucleic acid molecules including nucleotide sequences that are substantially identical (e.g., 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical) to the nucleotide sequence set forth as SEQ ID NO:1 or SEQ ID NO:3. The invention further features isolated nucleic acid molecules including at least 30, 35, 40, 45, 50, 75, 100, 125, 150, 175, 200, 250, 260, 300, 350, 372, 400, 450, 500, 550, 600, 615, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2260, 2300, 2350, 2400, 2450, 2500, 2550, 2600, 2650, 2700, 2750, 2800, 2825, 2850, 2875, 2900, 2950, 2960, or 2970 contiguous nucleotides of the nucleotide sequence set forth as SEQ ID NO:1 or SEQ ID NO:3. In another embodiment, the invention features isolated nucleic acid molecules which encode a polypeptide including an amino acid sequence that is substantially identical (e.g., 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical) to the amino acid sequence set forth as SEQ ID NO:2. The present invention also features nucleic acid molecules which encode allelic variants of the polypeptide having the amino acid sequence set forth as SEQ ID NO:2. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10, 15, 20, 25, 30, 35, 40, 45, 50, 75, 100, 125, 150, 175, 200, 250, 300, 350, 400, 450, 500, 550, 600, 604, 650, 700, 710, 716, 720, 730, 740, 750, 760, or 770 contiguous amino acid residues of the amino acid sequence of SEQ ID NO:2). In still other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., EPK-55053-encoding nucleic acid molecules). Such vectors can optionally include nucleotide sequences encoding heterologous polypeptides. Also featured are host cells including such vectors (e.g., host cells including vectors suitable for producing EPK-55053 nucleic acid molecules and polypeptides).

In another aspect, the invention features isolated EPK-55053 polypeptides and/or biologically active or antigenic fragments thereof. Exemplary embodiments feature a polypeptide including the amino acid sequence set forth as SEQ ID NO:2, a polypeptide including an amino acid sequence at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the amino acid sequence set forth as SEQ ID NO:2, a polypeptide encoded by a nucleic acid molecule including a nucleotide sequence at least 60%, 65%, 70%, 75%, 76%, 80%, 85%, 90%, 91%, 92%, 93%, 94%, 95%, 97%, 98%, 99%, 99.1%, 99.2%, 99.3%, 99.4%, 99.5%, 99.6%, 99.7%, 99.8%, or 99.9% identical to the nucleotide sequence set forth as SEQ ID NO:1 or SEQ ID NO:3. Also featured are fragments of the full-length polypeptides described herein (e.g., fragments including at least 10, 15, 20, 25, 30, 35, 40, 45, 50, 75, 100, 125, 150, 175, 200, 250, 300, 350, 400, 450, 500, 550, 600, 604, 650, 700, 710, 716, 720, 730, 740, 750, 760, or 770 contiguous amino acid residues of the sequence set forth as SEQ ID NO:2) as well as allelic variants of the polypeptide having the amino acid sequence set forth as SEQ ID NO:2.

The EPK-55053 polypeptides and/or biologically active or antigenic fragments thereof, are useful, for example, as reagents or targets in assays applicable to treatment and/or diagnosis of EPK-55053 mediated or related disorders. In one embodiment, an EPK-55053 polypeptide or fragment thereof, has an EPK-55053 activity. In another embodiment, an EPK-55053 polypeptide or fragment thereof, has a transmembrane domain, a eukaryotic protein kinase domain, a UBA domain, and, optionally, has an EPK-55053 activity. In a related aspect, the invention features antibodies (e.g., antibodies which specifically bind to any one of the polypeptides described herein) as well as fusion polypeptides including all or a fragment of a polypeptide described herein.

The present invention further features methods for detecting EPK-55053 polypeptides and/or EPK-55053 nucleic acid molecules, such methods featuring, for example, a probe, primer or antibody described herein. Also featured are kits for the detection of EPK-55053 polypeptides and/or EPK-55053 nucleic acid molecules. In a related aspect, the invention features methods for identifying compounds which bind to and/or modulate the activity of an EPK-55053 polypeptide or EPK-55053 nucleic acid molecule described herein. Further featured are methods for modulating an EPK-55053 activity.

Other features and advantages of the invention will be apparent from the following detailed description and claims.

BRIEF DESCRIPTION OF THE DRAWINGS

FIGS. 1A–1E depict the nucleotide sequence of the human EPK-55053 cDNA and the corresponding amino acid sequence. The nucleotide sequence corresponds to nucleic acids 1 to 2980 of SEQ ID NO:1. The amino acid sequence corresponds to amino acids 1–778 of SEQ ID NO:2. The coding region without the 5' or 3' untranslated regions of the human EPK-55053 gene is shown in SEQ ID NO:3.

FIGS. 3A-1–3A-3, 3B-1–3B-2, and 3C depict the results of a search which was performed against the Washington University HMM database and which resulted in the identification of a eukaryotic protein kinase domain (SEQ ID NO:5), a UBA domain (SEQ ID NO:6), a serkin_6 domain (SEQ ID NO:7), and a tyrkin_6 domain (SEQ ID NO:8) in the amino acid sequence of human EPK-55053 (SEQ ID NO:2).

DETAILED DESCRIPTION OF THE INVENTION

Figure 2:
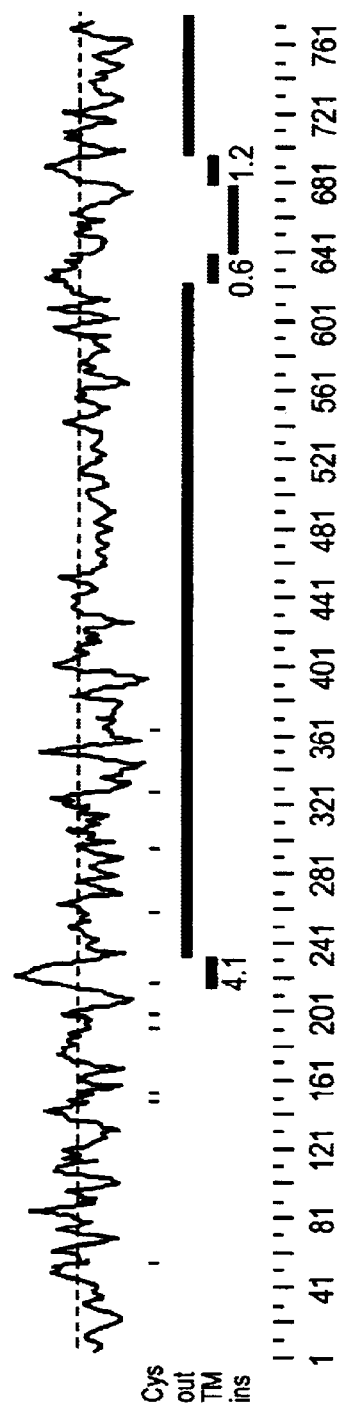
FIG. 2 depicts a structural, hydrophobicity, and antigenicity analysis of the human EK-1 protein.

The present invention is based, at least in part, on the discovery of novel members of a family of molecules, referred to herein as "Eukaryotic Protein Kinase-55053" or "EPK-55053" nucleic acid and polypeptide molecules. Members of this family of molecules are able to participate in the modulation of the phosphorylation state of EPK-55053 substrate molecules. By doing so, these molecules are able to contribute to the regulation and/or modulation of the activity of these substrate molecules, and, hence, the biochemical pathways with which the substrates are associated.

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., mouse or monkey polypeptides. Members of a family may also have common functional characteristics. The term "superfamily" is intended to mean two or more families of protein or nucleic acid molecules sharing conserved structural and/or functional features, but regulating, modulating, or participating in different cellular or physiological functions.

In one embodiment, the EPK-55053 molecules of the present invention include at least one "transmembrane domain." As used herein, the term "transmembrane domain" includes an amino acid sequence of about 20–45 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, alanines, valines, phenylalanines, prolines or methionines. Transmembrane domains are described in, for example, Zagotta W. N. et al. (1996) *Annu. Rev. Neurosci.* 19:235–263, the contents of which are incorporated herein by reference. Amino acid residues 214–231 of the human EPK-55053 polypeptide (SEQ ID NO:2) comprise a transmembrane domain (FIG. 2).

To identify the presence of a transmembrane domain in an EPK-55053 protein, and make the determination that a protein of interest has a particular profile, the amino acid sequence of the protein may be subjected to MEMSAT analysis. A MEMSAT analysis of the EPK-55053 protein set forth as SEQ ID NO:2 results in the identification of a transmembrane domain in the amino acid sequence of human EPK-55053 (SEQ ID NO:2) at about residues 214–231 (having a score of 4.1). Two other potential transmembrane domains were also identified at about amino acids 624–640 and 681–697 or SEQ ID NO:2.

In another embodiment, the EPK-55053 molecules of the present invention include at least one "eukaryotic protein kinase domain". As used herein, the term "eukaryotic protein kinase domain" includes a protein domain having at least about 150–350 amino acid residues and a bit score of at least 150 when compared against a eukaryotic protein kinase domain Hidden Markov Model (HMM), e.g., PFAM Accession Number PF00069. Preferably, a eukaryotic protein kinase domain includes a protein having an amino acid sequence of about 190–320, 210–300, 250–260 or more preferably about 252 amino acid residues, and a bit score of at least 150, 210, 250, 290, or more preferably, 323.4. To identify the presence of a eukaryotic protein kinase domain in an EPK-55053 protein, and make the determination that a protein of interest has a particular profile, the amino acid sequence of the protein may be searched against a database of known protein domains (e.g., the HMM database). The eukaryotic protein kinase domain has been assigned the PFAM Accession No. PF00069 (see the PFAM website, available through the University of Washington at St. Louis) and InterPro Accession No. IPR000719 (see the website for the European Bioinformatics Institute). A search was performed against the HMM database resulting in the identification of a eukaryotic protein kinase domain in the amino acid sequence of human EPK-55053 (SEQ ID NO:2) at about residues 34–285 of SEQ ID NO:2. The results of the search are set forth in FIGS. 3A-1–3A-3.

In another embodiment, the isolated nucleic acid molecules of the present invention encodes at least one "ubiquitin-associated domain" or "UBA domain" As used interchangeably herein, the terms "ubiquitin-associated domain" and "UBA domain" include a protein domain having at least about 10–70 amino acid residues when compared against a UBA domain Hidden Markov Model (HMM), e.g., PFAM Accession Number PF00627. Preferably, a UBA domain includes a protein having an amino acid sequence of about 10–70, 20–60, 30–50, 35–45 or more preferably about 40 amino acid residues, and a bit score of at least about 7.7. UBA domains (described in, for example, Diekmann et al. (1998) $Nat. Struct. Biol.$ 5:1042–1047) are domains that belong to an extensive family of proteins which share a conserved sequence and which have associations with ubiquitin and the ubiquitination pathway. To identify the presence of a UBA domain in an EPK-55053 protein, and make the determination that a protein of interest has a particular profile, the amino acid sequence of the protein may be searched against a database of known protein domains (e.g., the HMM database). The UBA domain has been assigned the PFAM Accession No. PF00627 (see the PFAM website, available through the University of Washington at St. Louis) and InterPro Accession No. IPR000449 (see the website for the European Bioinformatics Institute). A search was performed against the HMM database resulting in the identification of a UBA domain in the amino acid sequence of human EPK-55053 (SEQ ID NO:2) at about residues 315–356 of SEQ ID NO:2. The results of the search are set forth in FIGS. 3A-1—3A-3.

To elucidate the substrate specificity of the HPK-55053 proteins of the present invention, farther HMM analysis was performed using a proprietary database of Markov models, referred to herein as the SMART HMM database (see FIGS. 3A-1–3A-3, 3B-1–3B-2, and 3C). This analysis resulted in the identification of a serine threonine kinase ("serkin_6") domain at about amino acids 34–285 of the human EPK-55053 amino acid sequence set forth as SEQ ID NO-2. Notably, this serine/threonine kinase domain overlaps almost exclusively with the protein kinase domain identified by HMM searching of the PFAM database, identifying the instant proteins as serine/threonine kinases as compared to tyrosine kinases. This analysis also resulted in the identification of a tyrosine kinase domain ("tyrkin_6) at about amino acid residues 34-286 of SEQ ID NO:2.

Moreover, a signature sequence which is specific for serine/threonine kinases (consensus sequence given as SEQ ID NO:4) was identified at about residues 152–164 of SEQ ID NO:2. This signature sequence occurs in the central part of the kinase catalytic domain of serine/threonine kinases and contains a conserved aspartate residue which is important for the catalytic activity of the enzyme (Knighton D. R. et al. (1991) $Science$ 253:407–414). The consensus signature sequence described under the Prosite accession number PS00108 and is given as:

[LIVMFYC]-x-[HY]-x-D-[LIVMFY]-K-x(2)-N-[LIVMFYCT](3)
(SEQ ID NO:4)

A description of the Pfam database can be found in Sonhammer et al. (1997) $Proteins$ 28:405–420 and a detailed description of HMMs can be found, for example, in Gribskov et al.(1990) $Methods Enzymol.$ 183:146–159; Gribskov et al.(1987) $Proc. Natl. Acad. Sci. USA$ 84:4355–4358; Krogh et al.(1994) $J. Mol. Biol.$ 235:1501–1531; and Stultz et al.(1993) $Protein Sci.$ 2:305–314, the contents of which are incorporated herein by reference.

In a preferred embodiment, the EPK-55053 molecules of the invention include at least one transmembrane domain and/or at least one eukaryotic protein kinase domain, and/or at least one UBA domain.

Isolated EPK-55053 polypeptides of the present invention, have an amino acid sequence sufficiently identical to the amino acid sequence of SEQ ID NO:2 or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 60%, 65%, 70%, 75%, 76%, 80%, 85%, 90%, 91%, 92%, 93% 94%, 95%, 96%, 97%, 98%, 99%, 99.1%, 99.2%, 99.3%, 99.4%, 99.5%, 99.6%, 99.7%, 99.8%, 99.9% or more homology or identity across the amino acid sequences of the domains and contain at least one and preferably two structural domains or motifs, are defined herein as sufficiently identical. Furthermore, amino acid or nucleotide sequences which share at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homology or identity and share a common functional activity are defined herein as sufficiently identical.

In a preferred embodiment, an EPK-55053 polypeptide includes at least one or more of the following domains: a transmembrane domain, a eukaryotic protein kinase domain, a UBA domain, and has an amino acid sequence at least about 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homologous or identical to the amino acid sequence of SEQ ID NO:2. In yet another preferred embodiment, an EPK-55053 polypeptide includes at least one or more of the following domains: a transmembrane domain, a eukaryotic protein kinase domain, a UBA domain, and is encoded by a nucleic acid molecule having a nucleotide sequence which hybridizes under stringent hybridization conditions to a complement of a nucleic acid molecule comprising the nucleotide sequence of SEQ ID NO:1 or SEQ ID NO:3. In another preferred embodiment, an EPK-55053 polypeptide includes at least one or more of the following domains: a transmembrane domain, a eukaryotic protein kinase domain, a UBA domain, and has an EPK-55053 activity.

As used interchangeably herein, "EPK-55053 activity", "biological activity of EPK-55053" or "functional activity of EPK-55053", includes an activity exerted by an EPK-55053 polypeptide or nucleic acid molecule on an EPK-55053 responsive cell or tissue, or on an EPK-55053 polypeptide substrate, as determined in vivo, or in vitro, according to standard techniques. In one embodiment, an EPK-55053 activity is a direct activity, such as an association with an EPK-55053-target molecule. As used herein, a "target molecule" or "binding partner" is a molecule with which an EPK-55053 polypeptide binds or interacts in nature, such that EPK-55053-mediated function is achieved an EPK-55053 target molecule can be a non-EPK-55053 molecule, for example, a non-EPK-55053 polypeptide. Additional, exemplary EPK-55053 target molecules can include lipid moieties, a lipid-associated moiety, or a nucleic acid. In another embodiment, an EPK-55053 activity is an indirect activity, such as a cellular signaling activity mediated by interaction of the EPK-55053 polypeptide with an EPK-55053 ligand.

In a preferred embodiment, an EPK-55053 polypeptide has one or more of the following activities: (1) interaction with an EPK-55053 substrate or target molecule (e.g., a non-EPK-55053 protein); (2) conversion of an EPK-55053 substrate or target molecule to a product (e.g., transfer of a phosphate group to a substrate or target molecule, or conversion of ATP to ADP); (3) interaction with and/or phosphate transfer to a second non-EPK-55053 protein; (4) modulation of intra- or intercellular signaling and/or gene transcription (e.g., either directly or indirectly); (5) modulation of the phosphorylation state of EPK-55053 target molecules (e.g., a kinase or a phosphatase molecule) or the phosphorylation state of one or more proteins involved in cellular growth, metabolism, or differentiation, e.g., cardiac, epithelial, or neuronal cell growth or differentiation, as described in, for example, Lodish H. et al., *Molecular Cell Biology* (Scientific American Books Inc., New York, N.Y., 1995) and Stryer L., *Biochemistry* (W. H. Freeman, New York), the contents of which are incorporated herein by reference; (6) modulation of the activity of one or more proteins involved in cellular growth or differentiation, e.g., cardiac, epithelial, or neuronal cell growth or differentiation; (7) modulation of expression of one or more genes (e.g., a transcription factor); (8) modulation of signal transduction; and (9) participation in immunoregulation.

In other preferred embodiments, the EPK-55053 polypeptides of the present invention have one or more of the following activities: (1) modulation of cancer or tumor progression; (2) modulation of cellular proliferation; (3) modulation of tissue development (e.g., embryogenesis); (4) modulation of differentiation; (5) modulation of apoptosis; (6) modulation of energy metabolism; and (7) modulation of a ubiquitination pathway. Thus, the EPK-55053 molecules of the present invention can participate in: (1) the regulation of transmission of signals from cellular receptors, e.g., growth factor receptors; (2) the modulation of the entry of cells into mitosis; (3) the modulation of cellular differentiation; (4) the modulation of cell death; (5) the regulation of cytoskeleton function, e.g., actin bundling; and (6) metabolic pathways and the regulation of metabolic pathways.

The EPK-55053 molecules, by participating in the regulation of phosphorylation states, provide novel diagnostic targets and therapeutic agents for controlling or treating a variety of kinase associated disorders. As used herein, the term "kinase associated disorder" include disorders, diseases, or conditions which are characterized by aberrant, e.g., upregulated, downregulated, or misregulated, protein kinase levels. In a preferred embodiment, a kinase associated disorder includes the inhibition or over-stimulation of the activity of kinaaes involved in signaling pathways associated with cellular growth can lead to perturbed cellular growths which can in turn lead to cellular growth-related disorders. As used herein, a "cellular growth-related disorder", includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

Other examples of EPK-55053 associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, seizure disorders, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of EPK-55053 associated disorders include cardiac-related disorders. Cardiovascular system disorders in which the EPK-55053 molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. EPK-55053 associated disorders also include disorders of the musculoskeletal system such as paralysis and muscle weakness, e.g., ataxia, myotonia, and myokymia.

EPK-55053 associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

EPK-55053 associated or related disorders also include immune disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency.

EPK-55053 associated or related disorders also include disorders affecting tissues in which EPK-55053 protein is expressed.

The nucleotide sequence of the isolated human EPK-55053 cDNA and the predicted amino acid sequence of the human EPK-55053 polypeptide are shown in FIGS. 1A–1E and in SEQ ID NOs:1 and 2, respectively.

The human EPK-55053 gene, which is approximately 2980 nucleotides in length, encodes a polypeptide having a molecular weight of approximately 85.6 kD and which is approximately 778 amino acid residues in length.

Various aspects of the invention are described in further detail in the following subsections.

I. Isolated Nucleic Acid Molecules

One aspect of the invention pertains to isolated nucleic acid molecules that encode EPK-55053 proteins or biologically active portions thereof, as well as nucleic acid fragments sufficient for use as hybridization probes to identify EPK-55053-encoding nucleic acids (e.g., EPK-55053 mRNA) and fragments for use as PCR primers for the amplification or mutation of EPK-55053 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated EPK-55053 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. For example, using all or portion of the nucleic acid sequence of SEQ ID NO:1 or 3, as a hybridization probe, EPK-55053 nucleic acid molecules can be isolated using standard hybridization and cloning techniques (e.g., as described in Sambrook, J. et al., *Molecular Cloning: A Laboratory Manual.* 2nd ed, Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to EPK-55053 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1 or 3. This cDNA may comprise sequences encoding the human EPK-55053 protein (e.g., the "coding region", from nucleotides 86–2419), as well as 5' untranslated sequence (nucleotides 1–85) and 3' untranslated sequences (nucleotides 2420–2980) of SEQ ID NO:1. Alternatively, the nucleic acid molecule can comprise only the coding region of SEQ ID NO:1 (e.g., nucleotides 86–2419, corresponding to SEQ ID NO:3). Accordingly, in another embodiment, an isolated nucleic acid molecule of the invention comprises SEQ ID NO:3 and nucleotides 1–85 of SEQ ID NO:1. In yet another embodiment, the isolated nucleic acid molecule comprises SEQ ID NO:3 and nucleotides 2420–2980 of SEQ ID NO:1. In yet another embodiment, the nucleic acid molecule consists of the nucleotide sequence set forth as SEQ ID NO:1 or SEQ ID NO:3. In another embodiment, the nucleic acid molecule can comprise the coding region of SEQ ID NO:1 (e.g., nucleotides 86–2419, corresponding to SEQ ID NO:3), as well as a stop codon (e.g., nucleotides 2420–2422 of SEQ ID NO:1). In other embodiments, the nucleic acid molecule can comprise nucleotides 1–163,2423–2980, 1–52, 1–402, 952–2980,340–2980, 1–1802,2417–2980, 1–194, or 454–2980 of SEQ ID NO:1.

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3, respectively, such that it can hybridize to the nucleotide sequence shown in SEQ ID NO:1 or 3, respectively, thereby forming a stable duplex.

In still another preferred embodiment, an isolated nucleic acid molecule of the present invention comprises a nucleotide sequence which is at least about 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homologous to the nucleotide sequence (e.g., to the entire length of the nucleotide sequence) shown in SEQ ID NO:1 or 3, or a complement thereof, or a portion of any of these nucleotide sequences.

Moreover, the nucleic acid molecule of the invention can comprise only a portion of the nucleic acid sequence of SEQ ID NO:1 or 3, for example a fragment which can be used as a probe or primer or a fragment encoding a biologically active portion of an EPK-55053 protein. The nucleotide sequence determined from the cloning of the EPK-55053 gene allows for the generation of probes and primers designed for use in identifying and/or cloning other EPK-55053 family members, as well as EPK-55053 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, or of a naturally occurring allelic variant or mutant of SEQ ID NO:1 or 3. In an exemplary embodiment, a nucleic acid molecule of the present invention comprises a nucleotide sequence which is at least 30, 35, 40, 45, 50, 75, 100, 125, 150, 175, 200, 250, 260, 300, 350, 372, 400, 450, 500, 550, 600, 615, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2260, 2300, 2350, 2400, 2450, 2500, 2550, 2600, 2650, 2700, 2750, 2800, 2825, 2850, 2875, 2900, 2950, 2960, 2970, or more nucleotides in length and hybridizes under stringent hybridization conditions to a nucleic acid molecule of SEQ ID NO:1 or 3.

Probes based on the EPK-55053 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress an EPK-55053 protein, such as by measuring a level of an EPK-55053-encoding nucleic acid in a sample of cells from a subject e.g., detecting EPK-55053 mRNA levels or determining whether a genomic EPK-55053 gene has been mutated or deleted.

A nucleic acid fragment encoding a "biologically active portion of an EPK-55053 protein" can be prepared by isolating a portion of the nucleotide sequence of SEQ ID NO:1 or 3, which encodes a polypeptide having an EPK-55053 biological activity (the biological activities of the EPK-55053 proteins are described herein), expressing the encoded portion of the EPK-55053 protein (e.g., by recombinant expression in vitro) and assessing the activity of the encoded portion of the EPK-55053 protein.

The invention further encompasses nucleic acid molecules that differ from the nucleotide sequence shown in SEQ ID NO:1 or 3, or complements thereof, due to the degeneracy of the genetic code and, thus, encode the same EPK-55053 proteins as those encoded by the nucleotide sequence shown in SEQ ID NO:1 or 3. In another embodiment, an isolated nucleic acid molecule of the invention has a nucleotide sequence encoding an EPK-55053 protein.

In addition to the EPK-55053 nucleotide sequences shown in SEQ ID NO:1 or 3, it will be appreciated by those skilled in the art that DNA sequence polymorphisms that lead to changes in the amino acid sequences of the EPK-55053 proteins may exist within a population (e.g., the human population). Such genetic polymorphism in the EPK-55053 genes may exist among individuals within a population due to natural allelic variation. As used herein, the terms "gene" and "recombinant gene" refer to nucleic acid molecules which include an open reading frame encoding an EPK-55053 protein, preferably a mammalian EPK-55053 protein, and can further include non-coding regulatory sequences, and introns. Such natural allelic variations include both functional and non-functional EPK-55053 proteins and can typically result in 1–5% variance in the nucleotide sequence of an EPK-55053 gene. Any and all such nucleotide variations and resulting amino acid polymorphisms in EPK-55053 genes that are the result of natural allelic variation and that do not alter the functional activity of an EPK-55053 protein are intended to be within the scope of the invention.

Moreover, nucleic acid molecules encoding other EPK-55053 family members and, thus, which have a nucleotide sequence which differs from the EPK-55053 sequences of SEQ ID NO:1 or 3 are intended to be within the scope of the invention. For example, another EPK-55053 cDNA can be identified based on the nucleotide sequence of human EPK-55053. Moreover, nucleic acid molecules encoding EPK-55053 proteins from different species, and thus which have a nucleotide sequence which differs from the EPK-55053 sequences of SEQ ID NO:1 or 3 are intended to be within the scope of the invention. For example, a mouse EPK-55053 cDNA can be identified based on the nucleotide sequence of a human EPK-55053.

Nucleic acid molecules corresponding to natural allelic variants and homologues of the EPK-55053 cDNAs of the invention can be isolated based on their homology to the human EPK-55053 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 30, 35, 40, 45, 50, 75, 100, 125, 150, 175, 200, 250, 260, 300, 350, 372,400, 450, 500, 550, 600, 615, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2260, 2300, 2350, 2400, 2450, 2500, 2550, 2600, 2650, 2700, 2750, 2800, 2825, 2850, 2875, 2900, 2950, 2960, 2970 or more nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other.

Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65–70° C. (or alternatively hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or alternatively hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.1 5M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[$Na^+$])+0.41 (%G+C)-(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C. (see e.g., Church and Gilbert (1984) Proc. Natl. Acad Sci. USA 81:1991–1995), or alternatively 0.2×SSC, 1% SDS.

Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the EPK-55053 sequences that may exist in the population, the skilled artisan will further appreciate that changes can be introduced by mutation into the nucleotide sequences of SEQ ID NO:1 or 3, thereby leading to changes in the amino acid sequence of the encoded EPK-55053 proteins, without altering the functional ability of the EPK-55053 proteins. For example, nucleotide substitutions leading to amino acid substitutions at "non-essential" amino acid residues can be made in the sequence of an EPK-55053 protein. A "non-essential" amino acid residue is a residue that can be altered from the wild-type sequence of EPK-55053 without altering the biological activity, whereas an "essential" amino acid residue is required for biological activity. For example, amino acid residues that are conserved among the EPK-55053 proteins of the present invention, are predicted to be particularly unamenable to alteration. Furthermore, additional amino acid residues that are conserved between the EPK-55053 proteins of the present invention and other EPK-55053 family members are not likely to be amenable to alteration.

Accordingly, another aspect of the invention pertains to nucleic acid molecules encoding EPK-55053 proteins that contain changes in amino acid residues that are not essential for activity.

An isolated nucleic acid molecule encoding an EPK-55053 protein homologous to the EPK-55053 proteins of the present invention can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an EPK-55053 protein is preferably replaced with another amino acid residue from the same side chain family. Alternatively, in another embodiment, mutations can be introduced randomly along all or part of an EPK-55053 coding sequence, such as by saturation mutagenesis, and the resultant mutants can be screened for EPK-55053 biological activity to identify mutants that retain activity. Following mutagenesis of SEQ ID NO:1 or 3, the encoded protein can be expressed recombinantly and the activity of the protein can be determined.

In a preferred embodiment, a mutant EPK-55053 protein can be assayed for the ability to: (1) regulate transduction of signals from cellular receptors, e.g., growth factor receptors; (2) modulate the mitotic or meiotic state of cells (e.g., cell cycle regulation); (3) modulate cellular differentiation; (4) modulate cell death (e.g., apoptosis); (5) modulate cytoskeleton structure and/or function, e.g., actin bundling, or (6) participate in metabolic pathways and the regulation of metabolic pathways.

In addition to the nucleic acid molecules encoding EPK-55053 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire EPK-55053 coding strand, or only to a portion thereof. In one embodiment, an antisense nucleic acid molecule is antisense to a "coding region" of the coding strand of a nucleotide sequence encoding EPK-55053. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding EPK-55053. The term "noncoding region" refers to 5' and 3' sequences which flank the coding region that are not translated into amino acids (i.e., also referred to as 5' and 3' untranslated regions).

Given the coding strand sequences encoding EPK-55053 disclosed herein, antisense nucleic acids of the invention can be designed according to the rules of Watson and Crick base pairing. The antisense nucleic acid molecule can be complementary to the entire coding region of EPK-55053 mRNA, but more preferably is an oligonucleotide which is antisense to only a portion of the coding or noncoding region of EPK-55053 mRNA. For example, the antisense oligonucleotide can be complementary to the region surrounding the translation start site of EPK-55053 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an EPK-55053 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave EPK-55053 mRNA transcripts to thereby inhibit translation of EPK-55053 mRNA. A ribozyme having specificity for an EPK-55053-encoding nucleic acid can be designed based upon the nucleotide sequence of an EPK-55053 cDNA disclosed herein (i.e., SEQ ID NO:1 or 3). For example, a derivative of a Tetrahymena L-19 IVS RNA can be constructed in which the nucleotide sequence of the active site is complementary to the nucleotide sequence to be cleaved in an EPK-55053-encoding mRNA. See, e.g., Cech et al., U.S. Pat. No. 4,987,071; and Cech et al., U.S. Pat. No. 5,116,742. Alternatively, EPK-55053 mRNA can be used to select a catalytic RNA having a specific ribonuclease activity from a pool of RNA molecules. See, e.g., Bartel, D. and Szostak, J. W. (1993) *Science* 261:1411–1418.

Alternatively, EPK-55053 gene expression can be inhibited by targeting nucleotide sequences complementary to the regulatory region of the EPK-55053 (e.g., the EPK-55053 promoter and/or enhancers) to form triple helical structures that prevent transcription of the EPK-55053 gene in target cells. See generally, Helene, C. (1991) *Anticancer Drug Des.* 6(6):569–84; Helene, C. et al. (1992) *Ann. N. Y Acad Sci.* 660:27–36; and Maher, L. J. (1992) *Bioassays* 14(12):807-15.

In yet another embodiment, the EPK-55053 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med Chem.* 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670–675.

PNAs of EPK-55053 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of EPK-55053 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of EPK-55053 can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of EPK-55053 nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res*. 24 (17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res*. 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett*. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) *Bio-Techniques* 6:958–976) or intercalating agents (see, e.g., Zon (1988) *Pharm. Res*. 5:539–549). To this end, the oligonucleotide may be conjugated to another molecule (e.g., a peptide, hybridization triggered cross-linking agent, transport agent, or hybridization-triggered cleavage agent).

II. Isolated EPK-55053 Proteins and Anti-EPK-55053 Antibodies

One aspect of the invention pertains to isolated EPK-55053 proteins, and biologically active portions thereof, as well as polypeptide fragments suitable for use as immunogens to raise anti-EPK-55053 antibodies. In one embodiment, native EPK-55053 proteins can be isolated from cells or tissue sources by an appropriate purification scheme using standard protein purification techniques. In another embodiment, EPK-55053 proteins are produced by recombinant DNA techniques. Alternative to recombinant expression, an EPK-55053 protein or polypeptide can be synthesized chemically using standard peptide synthesis techniques.

An "isolated" or "purified" protein or biologically active portion thereof is substantially free of cellular material or other contaminating proteins from the cell or tissue source from which the EPK-55053 protein is derived, or substantially free from chemical precursors or other chemicals when chemically synthesized. The language "substantially free of cellular material" includes preparations of EPK-55053 protein in which the protein is separated from cellular components of the cells from which it is isolated or recombinantly produced. In one embodiment, the language "substantially free of cellular material" includes preparations of EPK-55053 protein having less than about 30% (by dry weight) of non-EPK-55053 protein (also referred to herein as a "contaminating protein"), more preferably less than about 20% of non-EPK-55053 protein, still more preferably less than about 10% of non-EPK-55053 protein, and most preferably less than about 5% non-EPK-55053 protein. When the EPK-55053 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of EPK-55053 protein in which the protein is separated from chemical precursors or other chemicals which are involved in the synthesis of the protein. In one embodiment, the language "substantially free of chemical precursors or other chemicals" includes preparations of EPK-55053 protein having less than about 30% (by dry weight) of chemical precursors or non-EPK-55053 chemicals, more preferably less than about 20% chemical precursors or non-EPK-55053 chemicals, still more preferably less than about 10% chemical precursors or non-EPK-55053 chemicals, and most preferably less than about 5% chemical precursors or non-EPK-55053 chemicals.

Biologically active portions of an EPK-55053 protein include peptides comprising amino acid sequences sufficiently homologous to or derived from the amino acid sequence of the EPK-55053 protein, which include fewer amino acids than the full length EPK-55053 proteins, and exhibit at least one activity of an EPK-55053 protein, as defined herein. Typically, biologically active portions comprise a domain or motif with at least one activity of the EPK-55053 protein. A biologically active portion of an EPK-55053 protein can be a polypeptide which is, for example, at least 10, 15, 20, 25, 30, 35, 40, 45, 50, 75, 100, 125, 150, 175, 200, 250, 300, 350, 400, 450, 500, 550, 600, 604, 650, 700, 710, 716, 720, 730, 740, 750, 760, or 770 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the EPK-55053 amino acid sequence of SEQ ID NO:2 having 778 amino acid residues, at least 233, preferably at least 311, more preferably at least 389, even more preferably at least 467, and even more preferably at least 545, 622, or 700 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at on line through the Genetics Computer Group), using either a Blosumn 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers, E. and Miller, W. (*Comput. Appl. Biosci.* 4:11–17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to EPK-55053 nucleic acid molecules of the invention. BLAST protein searches can be performed with the XBLAST program, score=100, wordlength=3, and a Blosum62 matrix to obtain amino acid sequences homologous to EPK-55053 polypeptide molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See the website for the National Center for Biotechnology Information.

The invention also provides EPK-55053 chimeric or fusion proteins. As used herein, an EPK-55053 "chimeric protein" or "fusion protein" comprises an EPK-55053 polypeptide operatively linked to a non-EPK-55053 polypeptide. An "EPK-55053 polypeptide" refers to a polypeptide having an amino acid sequence corresponding to EPK-55053, whereas a "non-EPK-55053 polypeptide" refers to a polypeptide having an amino acid sequence corresponding to a protein which is not substantially homologous to the EPK-55053 protein, e.g., a protein which is different from the EPK-55053 protein and which is derived from the same or a different organism. Within an EPK-55053 fusion protein the EPK-55053 polypeptide can correspond to all or a portion of an EPK-55053 protein. In a preferred embodiment, an EPK-55053 fusion protein comprises at least one biologically active portion of an EPK-55053 protein. In another preferred embodiment, an EPK-55053 fusion protein comprises at least two biologically active portions of an EPK-55053 protein. Within the fusion protein, the term "operatively linked" is intended to indicate that the EPK-55053 polypeptide and the non-EPK-55053 polypeptide are fused in-frame to each other. The non-EPK-55053 polypeptide can be fused to the N-terminus or C-terminus of the EPK-55053 polypeptide.

For example, in one embodiment, the fusion protein is a GST-EPK-55053 fusion protein in which the EPK-55053 sequences are fused to the C-terminus of the GST sequences. Such fusion proteins can facilitate the purification of recombinant EPK-55053.

In another embodiment, the fusion protein is an EPK-55053 protein containing a heterologous signal sequence at its N-terminus. In certain host cells (e.g., mammalian host cells), expression and/or secretion of EPK-55053 can be increased through use of a heterologous signal sequence.

The EPK-55053 fusion proteins of the invention can be incorporated into pharmaceutical compositions and administered to a subject in vivo. The EPK-55053 fusion proteins can be used to affect the bioavailability of an EPK-55053 substrate. Use of EPK-55053 fusion proteins may be useful therapeutically for the treatment of cellular growth related disorders, e.g., cancer. Moreover, the EPK-55053-fusion proteins of the invention can be used as immunogens to produce anti-EPK-55053 antibodies in a subject, to purify EPK-55053 ligands and in screening assays to identify molecules which inhibit the interaction of EPK-55053 with an EPK-55053 substrate.

Preferably, an EPK-55053 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). an EPK-55053-encoding nucleic acid can be cloned into such an expression vector such that the fusion moiety is linked in-frame to the EPK-55053 protein.

The present invention also pertains to variants of the EPK-55053 proteins which function as either EPK-55053 agonists (mimetics) or as EPK-55053 antagonists. Variants of the EPK-55053 proteins can be generated by mutagenesis, e.g., discrete point mutation or truncation of an EPK-55053 protein. An agonist of the EPK-55053 proteins can retain substantially the same, or a subset, of the biological activities of the naturally occurring form of an EPK-55053 protein. An antagonist of an EPK-55053 protein can inhibit one or more of the activities of the naturally occurring form of the EPK-55053 protein by, for example, competitively modulating a cellular activity of an EPK-55053 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the EPK-55053 protein.

In one embodiment, variants of an EPK-55053 protein which function as either EPK-55053 agonists (mimetics) or as EPK-55053 antagonists can be identified by screening combinatorial libraries of mutants, e.g., truncation mutants, of an EPK-55053 protein for EPK-55053 protein agonist or antagonist activity. In one embodiment, a variegated library of EPK-55053 variants is generated by combinatorial mutagenesis at the nucleic acid level and is encoded by a variegated gene library. A variegated library of EPK-55053 variants can be produced by, for example, enzymatically ligating a mixture of synthetic oligonucleotides into gene sequences such that a degenerate set of potential EPK-55053 sequences is expressible as individual polypeptides, or alternatively, as a set of larger fusion proteins (e.g., for phage display) containing the set of EPK-55053 sequences therein. There are a variety of methods which can be used to produce libraries of potential EPK-55053 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential EPK-55053 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477.

In addition, libraries of fragments of an EPK-55053 protein coding sequence can be used to generate a variegated population of EPK-55053 fragments for screening and subsequent selection of variants of an EPK-55053 protein. In one embodiment, a library of coding sequence fragments can be generated by treating a double stranded PCR fragment of an EPK-55053 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the EPK-55053 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of EPK-55053 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify EPK-55053 variants (Arkin and Youvan (1992) *Proc. Natl. Acad. Sci. USA* 89:7811–7815; Delagrave et al. (1993) *Protein Eng.* 6(3):327–331).

In one embodiment, cell based assays can be exploited to analyze a variegated EPK-55053 library. For example, a library of expression vectors can be transfected into a cell line which ordinarily synthesizes and secretes EPK-55053. The transfected cells are then cultured such that EPK-55053 and a particular mutant EPK-55053 are secreted and the effect of expression of the mutant on EPK-55053 activity in cell supernatants can be detected, e.g., by any of a number of enzymatic assays. Plasmid DNA can then be recovered from the cells which score for inhibition, or alternatively, potentiation of EPK-55053 activity, and the individual clones further characterized.

An isolated EPK-55053 protein, or a portion or fragment thereof, can be used as an immunogen to generate antibodies that bind EPK-55053 using standard techniques for polyclonal and monoclonal antibody preparation. A full-length EPK-55053 protein can be used or, alternatively, the invention provides antigenic peptide fragments of EPK-55053 for use as immunogens. The antigenic peptide of EPK-55053 comprises at least 8 amino acid residues and encompasses an epitope of EPK-55053 such that an antibody raised against the peptide forms a specific immune complex with EPK-55053. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of EPK-55053 that are located on the surface of the protein, e.g., hydrophilic regions.

An EPK-55053 immunogen typically is used to prepare antibodies by immunizing a suitable subject (e.g., rabbit, goat, mouse or other mammal) with the immunogen. An appropriate immunogenic preparation can contain, for example, recombinantly expressed EPK-55053 protein or a chemically synthesized EPK-55053 polypeptide. The preparation can further include an adjuvant, such as Freund's complete or incomplete adjuvant, or similar immunostimulatory agent. Immunization of a suitable subject with an immunogenic EPK-55053 preparation induces a polyclonal anti-EPK-55053 antibody response.

Accordingly, another aspect of the invention pertains to anti-EPK-55053 antibodies. The term "antibody" as used herein refers to immunoglobulin molecules and immunologically active portions of immunoglobulin molecules, i.e., molecules that contain an antigen binding site which specifically binds (immunoreacts with) an antigen, such as EPK-55053. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind EPK-55053. The term "monoclonal antibody" or "monoclonal antibody composition", as used herein, refers to a population of antibody molecules that contain only one species of an antigen binding site capable of immunoreacting with a particular epitope of EPK-55053. A monoclonal antibody composition thus typically displays a single binding affinity for a particular EPK-55053 protein with which it immunoreacts.

Polyclonal anti-EPK-55053 antibodies can be prepared as described above by immunizing a suitable subject with an EPK-55053 immunogen. The anti-EPK-55053 antibody titer in the immunized subject can be monitored over time by standard techniques, such as with an enzyme linked immunosorbent assay (ELISA) using immobilized EPK-55053. If desired, the antibody molecules directed against EPK-55053 can be isolated from the mammal (e.g., from the blood) and further purified by well known techniques, such as protein A chromatography to obtain the IgG fraction. At an appropriate time after immunization, e.g., when the anti-EPK-55053 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with an EPK-55053 immunogen as described above, and the culture supernatants of the resulting hybridoma cells are screened to identify a hybridoma producing a monoclonal antibody that binds EPK-55053.

Any of the many well known protocols used for fusing lymphocytes and immortalized cell lines can be applied for the purpose of generating an anti-EPK-55053 monoclonal antibody (see, e.g., Galfre, G. et al. (1977) *Nature* 266:55052; Gefter et al. (1977) supra; Lerner (1981) supra; Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from American Type Culture Collection (ATCC), 10801 University Boulevard, Manassas, Va. 20110–2209. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind EPK-55053, e.g., using a standard ELISA assay.

Alternative to preparing monoclonal antibody-secreting hybridomas, a monoclonal anti-EPK-55053 antibody can be identified and isolated by screening a recombinant combinatorial immunoglobulin library (e.g., an antibody phage display library) with EPK-55053 to thereby isolate immunoglobulin library members that bind EPK-55053. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al., PCT International Publication No. WO 92/01047; Garrard et al., PCT International Publication No. WO 92/09690; Ladner et al., PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad Sci. USA* 89:3576–3580; Garrard et al. (1991) *Bio/Technology* 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-EPK-55053 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Akira et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad Sci. USA* 84:214–218; Nishimura et al. (1987) *Cancer Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter, U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-EPK-55053 antibody (e.g., monoclonal antibody) can be used to isolate EPK-55053 by standard techniques, such as affinity chromatography or immunoprecipitation. An anti-EPK-55053 antibody can facilitate the purification of natural EPK-55053 from cells and of recombinantly produced EPK-55053 expressed in host cells. Moreover, an anti-EPK-55053 antibody can be used to detect EPK-55053 protein (e.g., in a cellular lysate or cell supernatant) in order to evaluate the abundance and pattern of expression of the EPK-55053 protein. Anti-EPK-55053 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodanmine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

III. Recombinant Expression Vectors and Host Cells

Another aspect of the invention pertains to vectors, preferably expression vectors, containing a nucleic acid encoding an EPK-55053 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., EPK-55053 proteins, mutant forms of EPK-55053 proteins, fusion proteins, and the like).

The recombinant expression vectors of the invention can be designed for expression of EPK-55053 proteins in prokaryotic or eukaryotic cells. For example, EPK-55053 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in EPK-55053 activity assays (e.g., direct assays or competitive assays described in detail below), or to generate antibodies specific for EPK-55053 proteins, for example. In a preferred embodiment, an EPK-55053 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al. (1988) *Gene* 69:301–315) and pET 11d (Studier et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the EPK-55053 expression vector is a yeast expression vector. Examples of vectors for expression in yeast *S. cerivisae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and picZ (Invitrogen Corp, San Diego, Calif.).

Alternatively, EPK-55053 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to EPK-55053 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an EPK-55053 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual* 2nd ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an EPK-55053 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (ie., express) an EPK-55053 protein. Accordingly, the invention further provides methods for producing an EPK-55053 protein using the host cells of the invention. In one embodiment, the method comprises culturing the host cell of invention (into which a recombinant expression vector encoding an EPK-55053 protein has been introduced) in a suitable medium such that an EPK-55053 protein is produced. In another embodiment, the method further comprises isolating an EPK-55053 protein from the medium or the host cell.

The host cells of the invention can also be used to produce non-human transgenic animals. For example, in one embodiment, a host cell of the invention is a fertilized oocyte or an embryonic stem cell into which EPK-55053-coding sequences have been introduced. Such host cells can then be used to create non-human transgenic animals in which exogenous EPK-55053 sequences have been introduced into their genome or homologous recombinant animals in which endogenous EPK-55053 sequences have been altered. Such animals are useful for studying the function and/or activity of an EPK-55053 and for identifying and/or evaluating modulators of EPK-55053 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous EPK-55053 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an EPK-55053-encoding nucleic acid into the male pronuclei of a fertilized oocyte, e.g., by microinjection, retroviral infection, and allowing the oocyte to develop in a pseudopregnant female foster animal. The EPK-55053 cDNA sequence of SEQ ID NO:1 or 3 can be introduced as a transgene into the genome of a non-human animal. Alternatively, a nonhuman homologue of a human EPK-55053 gene, such as a mouse or rat EPK-55053 gene, can be used as a transgene. Alternatively, an EPK-55053 gene homologue, such as another EPK-55053 family member, can be isolated based on hybridization to the EPK-55053 cDNA sequences of SEQ ID NO:1 or 3 (described further in subsection 1 above) and used as a transgene. Intronic sequences and polyadenylation signals can also be included in the transgene to increase the efficiency of expression of the transgene. A tissue-specific regulatory sequence(s) can be operably linked to an EPK-55053 transgene to direct expression of an EPK-55053 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of an EPK-55053 transgene in its genome and/or expression of EPK-55053 mRNA in tissues or cells of the animals. A transgenic founder animal can then be used to breed additional animals carrying the transgene. Moreover, transgenic animals carrying a transgene encoding an EPK-55053 protein can further be bred to other transgenic animals carrying other transgenes.

To create a homologous recombinant animal, a vector is prepared which contains at least a portion of an EPK-55053 gene into which a deletion, addition or substitution has been introduced to thereby alter, e.g., functionally disrupt, the EPK-55053 gene. The EPK-55053 gene can be a human gene (e.g., the SEQ ID NO:1 or 3), but more preferably, is a non-human homologue of a human EPK-55053 gene (e.g., a cDNA isolated by stringent hybridization with the nucleotide sequence of SEQ ID NO:1 or 3). For example, a mouse EPK-55053 gene can be used to construct a homologous recombination vector suitable for altering an endogenous EPK-55053 gene in the mouse genome. In a preferred embodiment, the vector is designed such that, upon homologous recombination, the endogenous EPK-55053 gene is functionally disrupted (i.e., no longer encodes a functional protein; also referred to as a "knock out" vector). Alternatively, the vector can be designed such that, upon homologous recombination, the endogenous EPK-55053 gene is mutated or otherwise altered but still encodes a functional protein (e.g., the upstream regulatory region can be altered to thereby alter the expression of the endogenous EPK-55053 protein). In the homologous recombination vector, the altered portion of the EPK-55053 gene is flanked at its 5' and 3' ends by additional nucleic acid sequence of the EPK-55053 gene to allow for homologous recombination to occur between the exogenous EPK-55053 gene carried by the vector and an endogenous EPK-55053 gene in an embryonic stem cell. The additional flanking EPK-55053 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51–503 for a description of homologous recombination vectors). The vector is introduced into an embryonic stem cell line (e.g., by electroporation) and cells in which the introduced FPK-55053 gene has homologously recombined with the endogenous EPK-55053 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, Robertson, E. J. ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/111354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The EPK-55053 nucleic acid molecules, EPK-55053 proteins, anti-EPK-55053 antibodies, and EPK-55053 modulators (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an EPK-55053 protein or anti-EPK-55053 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50(the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein.

When one or more of these small molecules is to be administered to an animal (e g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of EPK-55053 activity is administered in combination with other agents (e.g., a small molecule), or in conjunction with another, complementary treatment regime. For example, in one embodiment, a modulator of EPK-55053 activity is used to treat EPK-55053 associated disorder (e.g., a cellular proliferation, growth, apoptosis, differentiation, and/or migration disorder). Accordingly, modulation of EPK-55053 activity may be used in conjunction with, for example, another agent used to treat the disorder (e.g., chemotherapeutic agents such as 5-FU).

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chiorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthrarnycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al. "Monoclonal Antibodies for Immunotargeting of Drugs in Cancer Therapy" in *Monoclonal Antibodies and Cancer Therapy*, Reisfeld et al. (eds.), pp. 243–56 (Alan R. Liss, Inc. 1985); Hellstrom et al. "Antibodies for Drug Delivery" in *Controlled Drug Delivery* (2nd Ed.), Robinson et al. (eds.), pp. 623–53 (Marcel Dekker, Inc. 1987); Thorpe "Antibody Carriers of Cytotoxic Agents in Cancer Therapy: A Review" in *Monoclonal Antibodies '84: Biological and Clinical Applications*, Pinchera et al. (eds.), pp. 475–506 (1985); "Analysis, Results, And Future Prospective Of The Therapeutic Use of Radiolabeled Antibody in Cancer Therapy" in *Monoclonal Antibodies For Cancer Detection And Therapy*, Baldwin et al. (eds.), pp. 303–16 (Academic Press 1985); and Thorpe et al. "The Preparation and Cytotoxic Properties of Antibody-Toxin Conjugates" *Immunol. Rev.* 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, antibodies and/or modulators described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express EPK-55053 protein (e.g., via a recombinant expression vector in a host cell in gene therapy applications), to detect EPK-55053 mRNA (e.g., in a biological sample).or a genetic alteration in an EPK-55053 gene, and to modulate EPK-55053 activity, as described further below. The EPK-55053 proteins can be used to treat disorders characterized by insufficient or excessive production of an EPK-55053 substrate or production of EPK-55053 inhibitors. In addition, the EPK-55053 proteins can be used to screen for naturally occurring EPK-55053 substrates, to screen for drugs or compounds which modulate EPK-55053 activity, as well as to treat disorders characterized by insufficient or excessive production of EPK-55053 protein or production of EPK-55053 protein forms which have decreased or aberrant activity compared to EPK-55053 wild type protein. Moreover, the anti-EPK-55053 antibodies of the invention can be used to detect and isolate EPK-55053 proteins, regulate the bioavailability of EPK-55053 proteins, and modulate EPK-55053 activity.

A. Screening Assays:

The invention provides a method (also referred to herein as a "screening assay") for identifying modulators, ie., candidate or test compounds or agents (e.g., peptides, peptidomimetics, small molecules or other drugs) which bind to EPK-55053 proteins, have a stimulatory or inhibitory effect on, for example, EPK-55053 expression or EPK-55053 activity, or have a stimulatory or inhibitory effect on, for example, the expression or activity of an EPK-55053 substrate.

In one embodiment, the invention provides assays for screening candidate or test compounds which are substrates of an EPK-55053 protein or polypeptide or biologically active portion thereof. In another embodiment, the invention provides assays for screening candidate or test compounds which bind to or modulate the activity of an EPK-55053 protein or polypeptide or biologically active portion thereof, e.g., modulate the ability of EPK-55053 to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad Sci. USA* 87:6378–6382); (Felici (1991) *J. Mol. Biol.* 222:301–310); (Ladner supra.).

In another embodiment, an assay is a cell-based assay comprising contacting a cell expressing an EPK-55053 target molecule (e.g., an EPK-55053 phosphorylation substrate) with a test compound and determining the ability of the test compound to modulate (e.g., stimulate or inhibit) the activity of the EPK-55053 target molecule. Determining the ability of the test compound to modulate the activity of an EPK-55053 target molecule can be accomplished, for example, by determining the ability of the EPK-55053 protein to bind to or interact with the EPK-55053 target molecule, or by determining the ability of the EPK-55053 protein to phosphorylate the EPK-55053 target molecule.

The ability of the EPK-55053 protein to phosphorylate an EPK-55053 target molecule can be determined by, for example, an in vitro kinase assay. Briefly, an EPK-55053 target molecule, e.g., an immunoprecipitated EPK-55053 target molecule from a cell line expressing such a molecule, can be incubated with the EPK-55053 protein and radioactive ATP, e.g., $[\gamma\text{-}^{32}P]$ ATP, in a buffer containing $MgCl_2$ and $MnCl_2$, e.g., 10 mM $MgCl_2$ and 5 mM $MnCl_2$. Following the incubation, the immunoprecipitated EPK-55053 target molecule can be separated by SDS-polyacrylamide gel electrophoresis under educing conditions, transferred to a membrane, e.g., a PVDF membrane, and autoradiographed. The appearance of detectable bands on the autoradiograph indicates that the EPK-55053 substrate has been phosphorylated. Phosphoaminoacid analysis of the phosphorylated substrate can also be performed in order to determine which residues on the EPK-55053 substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the EPK-55053 protein to bind to or interact with an EPK-55053 target molecule can be accomplished by determining direct binding. Determining the ability of the EPK-55053 protein to bind to or interact with an EPK-55053 target molecule can be accomplished, for example, by coupling the EPK-55053 protein with a radioisotope or enzymatic label such that binding of the EPK-55053 protein to an EPK-55053 target molecule can be determined by detecting the labeled EPK-55053 protein in a complex. For example, EPK-55053 molecules, e.g., EPK-55053 proteins, can be labeled with $^{125}I$, $^{35}S$, $^{14}C$, or $^{3}H$, either directly or indirectly, and the radioisotope detected by direct counting of radioemission or by scintillation counting. Alternatively, EPK-55053 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between EPK-55053 and its target molecule, without the labeling of any of the interactants. For example, a microphysiometer can be used to detect the interaction of EPK-55053 with its target molecule without the labeling of either EPK-55053 or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the EPK-55053 protein to bind to or interact with an EPK-55053 target molecule can be accomplished by determining the activity of the target molecule. For example, the activity of the target molecule can be determined by detecting induction of a cellular second messenger of the target (e.g., ADP, intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which an EPK-55053 protein or biologically active portion thereof is contacted with a test compound and the ability of the test compound to bind to the EPK-55053 protein or biologically active portion thereof is determined. Binding of the test compound to the EPK-55053 protein can be determined either directly or indirectly as described above. In a preferred embodiment, the assay includes contacting the EPK-55053 protein or biologically active portion thereof with a known compound which binds EPK-55053 to form an assay mixture, contacting the assay mixture with a test compound, and determining the ability of the test compound to interact with an EPK-55053 protein, wherein determining the ability of the test compound to interact with an EPK-55053 protein comprises determining the ability of the test compound to preferentially bind to EPK-55053 or biologically active portion thereof as compared to the known compound.

In another embodiment, the assay is a cell-free assay in which an EPK-55053 protein or biologically active portion thereof is contacted with a test compound and the ability of the test compound to modulate (e.g., stimulate or inhibit) the activity of the EPK-55053 protein or biologically active portion thereof is determined. Determining the ability of the test compound to modulate the activity of an EPK-55053 protein can be accomplished, for example, by determining the ability of the EPK-55053 protein to bind to an EPK-55053 target molecule by one of the methods described above for determining direct binding. Determining the ability of the EPK-55053 protein to bind to an EPK-55053 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an EPK-55053 protein can be accomplished by determining the ability of the EPK-55053 protein to further modulate the activity of an EPK-55053 target molecule (e.g., an EPK-55053 mediated signal transduction pathway component). For example, the activity of the effector molecule on an appropriate target can be determined, or the binding of the effector to an appropriate target can be determined as previously described.

In yet another embodiment, the cell-free assay involves contacting an EPK-55053 protein or biologically active portion thereof with a known compound which binds the EPK-55053 protein to form an assay mixture, contacting the assay mixture with a test compound, and determining the ability of the test compound to interact with the EPK-55053 protein, wherein determining the ability of the test compound to interact with the EPK-55053 protein comprises determining the ability of the EPK-55053 protein to preferentially bind to or modulate the activity of an EPK-55053 target molecule.

The cell-free assays of the present invention are amenable to use of both soluble and/or membrane-bound forms of proteins (e.g., EPK-55053 proteins or biologically active portions thereof, or receptors to which EPK-55053 binds). In the case of cell-free assays in which a membrane-bound form a protein is used (e.g., a cell surface EPK-55053 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammuonio-1-propane sulfonate.

In more than one embodiment of the above assay methods of the present invention, it may be desirable to immobilize either EPK-55053 or its target molecule to facilitate separation of complexed from uncomplexed forms of one or both of the proteins, as well as to accommodate automation of the assay. Binding of a test compound to an EPK-55053 protein, or interaction of an EPK-55053 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/EPK-55053 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or EPK-55053 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of EPK-55053 binding or activity determined using standard techniques.

Other techniques for immobilizing proteins on matrices can also be used in the screening assays of the invention. For example, either an EPK-55053 protein or an EPK-55053 target molecule can be immobilized utilizing conjugation of biotin and streptavidin. Biotinylated EPK-55053 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with EPK-55053 protein or target molecules but which do not interfere with binding of the EPK-55053 protein to its target molecule can be derivatized to the wells of the plate, and unbound target or EPK-55053 protein trapped in the wells by antibody conjugation. Methods for detecting such complexes, in addition to those described above for the GST-immobilized complexes, include immunodetection of complexes using antibodies reactive with the EPK-55053 protein or target molecule, as well as enzyme-linked assays which rely on detecting an enzymatic activity associated with the EPK-55053 protein or target molecule.

In another embodiment, modulators of EPK-55053 expression are identified in a method wherein a cell is contacted with a candidate compound and the expression of EPK-55053 mRNA or protein in the cell is determined. The level of expression of EPK-55053 mRNA or protein in the presence of the candidate compound is compared to the level of expression of EPK-55053 mRNA or protein in the absence of the candidate compound. The candidate compound can then be identified as a modulator of EPK-55053 expression based on this comparison. For example, when expression of EPK-55053 mRNA or protein is greater (statistically significantly greater) in the presence of the candidate compound than in its absence, the candidate compound is identified as a stimulator of EPK-55053 mRNA or protein expression. Alternatively, when expression of EPK-55053 mRNA or protein is less (statistically significantly less) in the presence of the candidate compound than in its absence, the candidate compound is identified as an inhibitor of EPK-55053 mRNA or protein expression. The level of EPK-55053 mRNA or protein expression in the cells can be determined by methods described herein for detecting EPK-55053 mRNA or protein.

In yet another aspect of the invention, the EPK-55053 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with EPK-55053 ("EPK-55053-binding proteins" or "EPK-55053-bp") and are involved in EPK-55053 activity. Such EPK-55053-binding proteins are also likely to be involved in the propagation of signals by the EPK-55053 proteins or EPK-55053 targets as, for example, downstream elements of an EPK-55053-mediated signaling pathway. Alternatively, such EPK-55053-binding proteins are likely to be EPK-55053 inhibitors.

The two-hybrid system is based on the modular nature of most transcription factors, which consist of separable DNA-binding and activation domains. Briefly, the assay utilizes two different DNA constructs. In one construct, the gene that codes for an EPK-55053 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an EPK-55053-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the EPK-55053 protein.

This invention further pertains to novel agents identified by the above-described screening assays. Accordingly, it is within the scope of this invention to further use an agent identified as described herein in an appropriate animal model. For example, an agent identified as described herein (e.g., an EPK-55053 modulating agent, an antisense EPK-55053 nucleic acid molecule, an EPK-55053-specific antibody, or an EPK-55053-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the EPK-55053 nucleotide sequences, described herein, can be used to map the location of the EPK-55053 genes on a chromosome. The mapping of the EPK-55053 sequences to chromosomes is an important first step in correlating these sequences with genes associated with disease.

Briefly, EPK-55053 genes can be mapped to chromosomes by preparing PCR primers (preferably 15–25 bp in length) from the EPK-55053 nucleotide sequences. Computer analysis of the EPK-55053 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the EPK-55053 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the EPK-55053 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature* 325:783–787.

Moreover, differences in the DNA sequences between individuals affected and unaffected with a disease associated with the EPK-55053 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The EPK-55053 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the EPK-55053 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The EPK-55053 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 3, can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from EPK-55053 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial EPK-55053 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the EPK-55053 nucleotide sequences or portions thereof having a length of at least 20 bases, preferably at least 30 bases.

The EPK-55053 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such EPK-55053 probes can be used to identify tissue by species and/or by organ type.

In a similar fashion, these reagents, e.g., EPK-55053 primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining EPK-55053 protein and/or nucleic acid expression as well as EPK-55053 activity, in the context of a biological sample (e.g., blood, serum, cells, tissue) to thereby determine whether an individual is afflicted with a disease or disorder, or is at risk of developing a disorder, associated with aberrant EPK-55053 expression or activity (e.g., a kinase associated disorder, a cellular growth-related disorder). The invention also provides for prognostic (or predictive) assays for determining whether an individual is at risk of developing a disorder associated with EPK-55053 protein, nucleic acid expression or activity. For example, mutations in an EPK-55053 gene can be assayed in a biological sample. Such assays can be used for prognostic or predictive purpose to thereby prophylactically treat an individual prior to the onset of a disorder characterized by or associated with EPK-55053 protein, nucleic acid expression or activity.

Another aspect of the invention pertains to monitoring the influence of agents (e.g., drugs, compounds) on the expression or activity of EPK-55053 in clinical trials.

These and other agents are described in further detail in the following sections.

1. Diagnostic Assays

An exemplary method for detecting the presence or absence of EPK-55053 protein or nucleic acid in a biological sample involves obtaining a biological sample from a test subject and contacting the biological sample with a compound or an agent capable of detecting EPK-55053 protein or nucleic acid (e.g., mRNA, genomic DNA) that encodes EPK-55053 protein such that the presence of EPK-55053 protein or nucleic acid is detected in the biological sample. A preferred agent for detecting EPK-55053 mRNA or genomic DNA is a labeled nucleic acid probe capable of hybridizing to EPK-55053 mRNA or genomic DNA. The nucleic acid probe can be, for example, a human EPK-55053 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to EPK-55053 mRNA or genomic DNA. Other suitable probes for use in the diagnostic assays of the invention are described herein.

A preferred agent for detecting EPK-55053 protein is an antibody capable of binding to EPK-55053 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect EPK-55053 mRNA, protein, or genomic DNA in a biological sample in vitro as well as in viva. For example, in vitro techniques for detection of EPK-55053 mRNA include Northern hybridizations and in situ hybridizations. In vitro techniques for detection of EPK-55053 protein include enzyme linked immunosorbent assays (ELISAs), Western blots, immunoprecipitations and immunofluorescence. In vitro techniques for detection of EPK-55053 genomic DNA include Southern hybridizations. Furthermore, in vivo techniques for detection of EPK-55053 protein include introducing into a subject a labeled anti-EPK-55053 antibody. For example, the antibody can be labeled with a radioactive marker whose presence and location in a subject can be detected by standard imaging techniques.

In one embodiment, the biological sample contains protein molecules from the test subject Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting EPK-55053 protein, mRNA, or genomic DNA, such that the presence of EPK-55053 protein, mRNA or genomic DNA is detected in the biological sample, and comparing the presence of EPK-55053 protein, mRNA or genomic DNA in the control sample with the presence of EPK-55053 protein, mRNA or genomic DNA in the test sample.

The invention also encompasses kits for detecting the presence of EPK-55053 in a biological sample. For example, the kit can comprise a labeled compound or agent capable of detecting EPK-55053 protein or mRNA in a biological sample; means for determining the amount of EPK-55053 in the sample; and means for comparing the amount of EPK-55053 in the sample with a standard. The compound or agent can be packaged in a suitable container. The kit can further comprise instructions for using the kit to detect EPK-55053 protein or nucleic acid.

2. Prognostic Assays

The diagnostic methods described herein can furthermore be utilized to identify subjects having or at risk of developing a disease or disorder associated with aberrant EPK-55053 expression or activity. For example, the assays described herein, such as the preceding diagnostic assays or the following assays, can be utilized to identify a subject having or at risk of developing a disorder associated with EPK-55053 protein, nucleic acid expression or activity (e.g., a kinase associated disorder, a cellular growth-related disorder). Thus, the present invention provides a method for identifying a disease or disorder associated with aberrant EPK-55053 expression or activity in which a test sample is obtained from a subject and EPK-55053 protein or nucleic acid (e.g., mRNA, genomic DNA) is detected, wherein the presence of EPK-55053 protein or nucleic acid is diagnostic for a subject having or at risk of developing a disease or disorder associated with aberrant EPK-55053 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant EPK-55053 expression or activity. Thus, the present invention provides methods for determining whether a subject can be effectively treated with an agent for a disorder associated with aberrant EPK-55053 expression or activity in which a test sample is obtained and EPK-55053 protein or nucleic acid expression or activity is detected (e.g., wherein the abundance of EPK-55053 protein or nucleic acid expression or activity is diagnostic for a subject that can be administered the agent to treat a disorder associated with aberrant EPK-55053 expression or activity).

The methods of the invention can also be used to detect genetic alterations in an EPK-55053 gene, thereby determining if a subject with the altered gene is at risk for a disorder associated with the EPK-55053 gene. In preferred embodiments, the methods include detecting, in a sample of cells from the subject, the presence or absence of a genetic alteration characterized by at least one of an alteration affecting the integrity of a gene encoding an EPK-55053-protein, or the mis-expression of the EPK-55053 gene. For example, such genetic alterations can be detected by ascertaining the existence of at least one of 1) a deletion of one or more nucleotides from an EPK-55053 gene; 2) an addition of one or more nucleotides to an EPK-55053 gene; 3) a substitution of one or more nucleotides of an EPK-55053 gene, 4) a chromosomal rearrangement of an EPK-55053 gene; 5) an alteration in the level of a messenger RNA transcript of an EPK-55053 gene, 6) aberrant modification of an EPK-55053 gene, such as of the methylation pattern of the genomic DNA, 7) the presence of a non-wild type splicing pattern of a messenger RNA transcript of an EPK-55053 gene, 8) a non-wild type level of an EPK-55053-protein, 9) allelic loss of an EPK-55053 gene, and 10) inappropriate post-translational modification of an EPK-55053-protein. As described herein, there are a large number of assay techniques known in the art which can be used for detecting alterations in an EPK-55053 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the EPK-55053-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an EPK-55053 gene under conditions such that hybridization and amplification of the EPK-55053-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad Sci. USA* 87:1874–1878), transcriptional amplification system (Kwoh, D. Y. et al. (1989) *Proc. Natl. Acad. Sci USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an EPK-55053 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in EPK-55053 can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244–255; Kozal, M. J. et al. (1996) *Nat. Med.* 2:753–759). For example, genetic mutations in EPK-55053 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the EPK-55053 gene and detect mutations by comparing the sequence of the sample EPK-55053 with the corresponding wild-type (control) sequence. Examples of sequencing reactions include those based on techniques developed by Maxam and Gilbert ((1977) *Proc. Natl. Acad Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g. PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the EPK-55053 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type EPK-55053 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in EPK-55053 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an EPK-55053 sequence, e.g. a wild-type EPK-55053 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in EPK-55053 genes. For example, single strand conformation polymorphism (SSCP) may be used to detect differences in electrophoretic mobility between mutant and wild type nucleic acids (Orita et al. (1989) *Proc. Natl. Acad. Sci USA* 86:2766, see also Cotton (1993) *Mutat. Res.* 285:125–144; and Hayashi (1992) *Genet. Anal. Tech. Appl.* 9:73–79). Single-stranded DNA fragments of sample and control EPK-55053 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an EPK-55053 gene.

Furthermore, any cell type or tissue in which EPK-55053 is expressed may be utilized in the prognostic assays described herein.

3. Monitoring of Effects During Clinical Trials

Monitoring the influence of agents (e.g., drugs or compounds) on the expression or activity of an EPK-55053 protein can be applied not only in basic drug screening, but also in clinical trials. For example, the effectiveness of an agent determined by a screening assay as described herein to increase EPK-55053 gene expression, protein levels, or upregulate EPK-55053 activity, can be monitored in clinical trials of subjects exhibiting decreased EPK-55053 gene expression, protein levels, or downregulated EPK-55053 activity. Alternatively, the effectiveness of an agent determined by a screening assay to decrease EPK-55053 gene expression, protein levels, or downregulate EPK-55053 activity, can be monitored in clinical trials of subjects exhibiting increased EPK-55053 gene expression, protein levels, or upregulated EPK-55053 activity. In such clinical trials, the expression or activity of an EPK-55053 gene, and preferably, other genes that have been implicated in a disorder can be used as a "read out" or markers of the phenotype of a particular cell.

For example, and not by way of limitation, genes, including EPK-55053, that are modulated in cells by treatment with an agent (e.g., compound, drug or small molecule) which modulates EPK-55053 activity (e.g., identified in a screening assay as described herein) can be identified. Thus, to study the effect of agents on an EPK-55053 associated disorder, for example, in a clinical trial, cells can be isolated and RNA prepared and analyzed for the levels of expression of EPK-55053 and other genes implicated in the EPK-55053 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of EPK-55053 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of an EPK-55053 protein, mRNA, or genomic DNA in the pre-administration sample; (iii) obtaining one or more post-administration samples from the subject; (iv) detecting the level of expression or activity of the EPK-55053 protein, mRNA, or genomic DNA in the post-administration samples; (v) comparing the level of expression or activity of the EPK-55053 protein, mRNA, or genomic DNA in the pre-administration sample with the EPK-55053 protein, mRNA, or genomic DNA in the post administration sample or samples; and (vi) altering the administration of the agent to the subject accordingly. For example, increased administration of the agent may be desirable to increase the expression or activity of EPK-55053 to higher levels than detected, i.e., to increase the effectiveness of the agent. Alternatively, decreased administration of the agent may be desirable to decrease expression or activity of EPK-55053 to lower levels than detected, i.e., to decrease the effectiveness of the agent. According to such an embodiment, EPK-55053 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant EPK-55053 expression or activity (e.g., a kinase associated disorder, a cellular growth-related disorder). "Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the EPK-55053 molecules of the present invention or EPK-55053 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant EPK-55053 expression or activity, by administering to the subject an EPK-55053 or an agent which modulates EPK-55053 expression or at least one EPK-55053 activity. Subjects at risk for a disease which is caused or contributed to by aberrant EPK-55053 expression or activity can be identified by, for example, any or a combination of diagnostic or prognostic assays as described herein. Administration of a prophylactic agent can occur prior to the manifestation of symptoms characteristic of the EPK-55053 aberrancy, such that a disease or disorder is prevented or, alternatively, delayed in its progression. Depending on the type of EPK-55053 aberrancy, for example, an EPK-55053, EPK-55053 agonist or EPK-55053 antagonist agent can be used for treating the subject. The appropriate agent can be determined based on screening assays described herein.

2. Therapeutic Methods

Another aspect of the invention pertains to methods of modulating EPK-55053 expression or activity for therapeutic purposes. Accordingly, in an exemplary embodiment, the modulatory method of the invention involves contacting a cell with an EPK-55053 or agent that modulates one or more of the activities of EPK-55053 protein activity associated with the cell. An agent that modulates EPK-55053 protein activity can be an agent as described herein, such as a nucleic acid or a protein, a naturally-occurring target molecule of an EPK-55053 protein (e.g., an EPK-55053 phosphorylation substrate), an EPK-55053 antibody, an EPK-55053 agonist or antagonist, a peptidomimetic of an EPK-55053 agonist or antagonist, or other small molecule. In one embodiment, the agent stimulates one or more EPK-55053 activities. Examples of such stimulatory agents include active EPK-55053 protein and a nucleic acid molecule encoding EPK-55053 that has been introduced into the cell. In another embodiment, the agent inhibits one or more EPK-55053 activities. Examples of such inhibitory agents include antisense EPK-55053 nucleic acid molecules, anti-EPK-55053 antibodies, and EPK-55053 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an EPK-55053 protein or nucleic acid molecule. In one embodiment, the method involves administering an agent (e.g., an agent identified by a screening assay described herein), or combination of agents that modulates (e.g., upregulates or downregulates) EPK-55053 expression or activity. In another embodiment, the method involves administering an EPK-55053 protein or nucleic acid molecule as therapy to compensate for reduced or aberrant EPK-55053 expression or activity.

Stimulation of EPK-55053 activity is desirable in situations in which EPK-55053 is abnormally downregulated and/or in which increased EPK-55053 activity is likely to have a beneficial effect. For example, stimulation of EPK-55053 activity is desirable in situations in which an EPK-55053 is downregulated and/or in which increased EPK-55053 activity is likely to have a beneficial effect. Likewise, inhibition of EPK-55053 activity is desirable in situations in which EPK-55053 is abnormally upregulated and/or in which decreased EPK-55053 activity is likely to have a beneficial effect.

3. Pharmacogenomics

The EPK-55053 molecules of the present invention, as well as agents, or modulators which have a stimulatory or inhibitory effect on EPK-55053 activity (e.g., EPK-55053 gene expression) as identified by a screening assay described herein can be administered to individuals to treat (prophylactically or therapeutically) disorders (e.g., proliferative disorders such as cancer) associated with aberrant EPK-55053 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an EPK-55053 molecule or EPK-55053 modulator as well as tailoring the dosage and/or therapeutic regimen of treatment with an EPK-55053 molecule or EPK-55053 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., an EPK-55053 protein or EPK-55053 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an EPK-55053 molecule or EPK-55053 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an EPK-55053 molecule or EPK-55053 modulator, such as a modulator identified by one of the exemplary screening assays described herein.

4. Use of EPK-55053 Molecules as Surrogate Markers

The EPK-55053 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the EPK-55053 molecules of the invention may be detected, and may be correlated with one or more biological states in vivo. For example, the EPK-55053 molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258–264; and James (1994) *AIDS Treatment News Archive* 209.

The EPK-55053 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an EPK-55053 marker) transcription or expression, the amplified marker may be in a quantity which is more readily detectable than the drug itself. Also, the marker may be more easily detected due to the nature of the marker itself; for example, using the methods described herein, anti-EPK-55053 antibodies may be employed in an immune-based detection system for an EPK-55053 protein marker, or EPK-55053-specific radiolabeled probes may be used to detect an EPK-55053 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al., U.S. Pat. No. 6,033,862; Hattis et al. (1991) *Env. Health Perspect.* 90:229–238; Schentag (1999) *Am. J. Health-Syst. Pharm.* 56 Suppl. 3:S21–S24; and Nicolau (1999) *Am. J. Health-Syst. Pharm.* 56 Suppl. 3:S16–S20.

The EPK-55053 molecules of the invention are also useful as pharmacogenomic markers. As used herein, a "pharmacogenomic marker" is an objective biochemical marker which correlates with a specific clinical drug response or susceptibility in a subject (see, e.g., McLeod et at. (1999) *Eur. J. Cancer* 35(12):1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., EPK-55053 protein or RNA) for specific tumor markers in a subject, a drug or course of treatment may be selected that is optimized for the treatment of the specific tumor likely to be present in the subject. Similarly, the presence or absence of a specific sequence mutation in EPK-55053 DNA may correlate EPK-55053 drug response. The use of pharmacogenomic markers therefore permits the application of the most appropriate treatment for each subject without having to administer the therapy.

E. Electronic Apparatus Readable Media and Arrays

Electronic apparatus readable media comprising EPK-55053 sequence information is also provided. As used herein, "EPK-55053 sequence information" refers to any nucleotide and/or amino acid sequence information particular to the EPK-55053 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said EPK-55053 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon EPK-55053 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the EPK-55053 sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the EPK-55053 sequence information.

By providing EPK-55053 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a kinase associated disease or disorder or a pre-disposition to a kinase associated disorder, wherein the method comprises the steps of determining EPK-55053 sequence information associated with the subject and based on the EPK-55053 sequence information, determining whether the subject has a kinase associated disorder or a pre-disposition to a kinase associated disorder, and/or recommending a particular treatment for the disease, disorder, or pre-disease condition.

The present invention further provides in an electronic system and/or in a network, a method for determining whether a subject has a kinase associated disorder or a pre-disposition to a kinase associated disorder wherein the method comprises the steps of determining EPK-55053 sequence information associated with the subject, and based on the EPK-55053 sequence information, determining whether the subject has a kinase associated disorder or a pre-disposition to a kinase associated disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a kinase associated disorder or a pre-disposition to a kinase associated disorder associated with EPK-55053, said method comprising the steps of receiving EPK-55053 sequence information from the subject and/or information related thereto, receiving phenotypic information associated with the subject, acquiring information from the network corresponding to EPK-55053 and/or a kinase associated disorder, and based on one or more of the phenotypic information, the EPK-55053 information (e.g., sequence information and/or information related thereto), and the acquired information, determining whether the subject has a kinase associated disorder or a pre-disposition to a kinase associated disorder. The method may further comprise the step of recommending a particular treatment for the disease, disorder or pre-disease condition.

The present invention also provides a business method for determining whether a subject has a kinase associated disorder or a predisposition to a kinase associated disorder, said method comprising, the steps of receiving information related to EPK-55053 (e.g., sequence information and/or information related thereto), receiving phenotypic information associated with the subject, acquiring information from the network related to EPK-55053 and/or related to a kinase associated disorder, and based on one or more of the phenotypic information, the EPK-55053 information, and the acquired information, determining whether the subject has a kinase associated or a pre-disposition to a kinase associated disorder. The method may further comprise the step of recommending a particular treatment for the disease, disorder or pre-disease condition.

The invention also includes an array comprising an EPK-55053 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be EPK-55053. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a kinase associated disorder, progression of a kinase associated disorder, and processes, such a cellular transformation associated with the kinase associated disorder.

The array is also useful for ascertaining the effect of the expression of a gene on the expression of other genes in the same cell or in different cells (e.g., ascertaining the effect of EPK-55053 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including EPK-55053) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Identification and Characterization of Human EPK-55053 cDNA

In this example, the identification and characterization of the gene encoding human EPK-55053 (clone 55053) is described.

Isolation of the Human EPK-55053 cDNA

The invention is based, at least in part, on the discovery of a human gene encoding a novel polypeptide, referred to herein as human EPK-55053. The entire sequence of the human clone 55053 was determined and found to contain an open reading frame termed human "EPK-55053." The nucleotide sequence of the human EPK-55053 gene is set forth in FIGS. 1A–1E and in the Sequence Listing as SEQ ID NO:1. The amino acid sequence of the human EPK-55053 expression product is set forth in FIGS. 1A–1E and in the Sequence Listing as SEQ ID NO:2. The EPK-55053 polypeptide comprises about 778 amino acids. The coding region (open reading frame) of SEQ ID NO:1 is set forth as SEQ ID NO:3.

Analysis of the Human EPK-55053 Molecules

A search using the polypeptide sequence of SEQ ID NO:2 was performed against the HMM database in PFAM (FIGS. 3A-1–3A-3) resulting in the identification of a eukaryotic protein kinase domain in the amino acid sequence of human EPK-55053 at about residues 34–285 of SEQ ID NO:2 (score=323.4). Searching the SMART HMM database resulted in the further identification of this domain as a serine threonine kinase domain (FIGS. 3A-1–3A-3,3B-1–3B-2, and 3C).

This search also resulted in the identification of a UBA domain in the amino acid sequence of human EPK-55053 at about residues 315–356 of SEQ ID NO:2 (score=7.7) (FIGS. 3A-1–3A-3).

A search using the polypeptide sequence of SEQ ID NO:2 was also performed against the Memsat database (FIG. 2), resulting in the identification of potential transmembrane domains (score=4.1) in the amino acid sequence of human EPK-55053 (SEQ ID NO:2) at about residues 214–231, 624–640, and 681–697.

Searches of the amino acid sequence of human EPK-55053 were further performed against the Prosite database. These searches resulted in the identification in the amino acid sequence of human EPK-55053 of a potential cAMP/cGMP-dependant protein kinase phosphorylation site (ProSite Accession No. PS00004) at about residues 272–275 of SEQ ID NO:2. A glycosaminoglycan attachment site (ProSite Accession No. PS00002) was also identified at about residues 682–685. Fifteen potential protein kinase C phosphorylation sites (ProSite Accession No. PS00005) were identified at about residues 129–131, 417–419, 427–429, 447–449, 472–474, 496–498, 508–510, 523–525, 555–557, 563–565, 619–621, 643–645, 676–678, 699–701, and 758–760 of SEQ ID NO:2. Twelve potential casein kinase II sites (ProSite Accession No. PS00006) were identified at about residues 114–117, 129–132, 142–145, 185–188, 311–314,341–344, 363–366, 404–407, 575–578, 586–589, 668–671, and 715–718 of SEQ ID NO:2. Eleven potential N-myristoylation sites (ProSite Accession No. PS00008) were identified at about residues 4–9, 10–15, 57–62, 435–440, 468–473, 485–490, 507–512, 530–535, 541–546, 597–602, and 681–686 of SEQ ID NO:2. Three amidation sites (ProSite Accession No. PS00009) were identified at about residues 208–211, 300–303, and 390–393 of SEQ ID NO:2. Most notably, serine/threonine protein kinase active site signature (ProSite Accession No. PS00108) was identified at about residues 152–164.

The amino acid sequence of human EPK-55053 was analyzed using the program PSORT (available online; see Nakai, K. and Kanehisa, M. (1992) *Genomics* 14:897–911) to predict the localization of the proteins within the cell. This program assesses the presence of different targeting and localization amino acid sequences within the query sequence. The results of the analyses show that human EPK-55053 may be localized to the cytoplasm, nucleus, or mitochondria.

Further homologies of interest were identified by using the amino acid sequence of EPK-55053 (SEQ ID NO:2) to search the ProDom database (available through the Institute National de la Recherche Agronomique, France). This search resulted in the identification of homology in the amino acid sequence of human EPK-55053 to a yeast probable serine/threonine protein kinase, a hypothetical 169.2 kD protein, a transmembrane kinase protein, a putative NPK-1 kinase, a *C. elegans* serine/threonine protein kinase, and HRPOPK-1 protein.

Tissue Distribution of Human EPK-55053 mRNA

This example describes the tissue distribution of human EPK-55053 mRNA, as may be determined by in situ hybridization analysis using oligonucleotide probes based on the human EPK-55053 sequence.

For in situ analysis, various tissues, e.g., tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5 \times 10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 g of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant EPK-55053 Proteins in Bacterial Cells

In this example, human kinases of the present invention are expressed as recombinant glutathione-S-transferase (GST) fusion polypeptides in *E. coli* and the fusion polypeptide is isolated and characterized. Specifically, kinases are fused to GST and this fusion polypeptide is expressed in *E. coli*, e.g., strain PEB199. Expression of the GST-EPK-55053 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant EPK-55053 Proteins in COS Cells

To express the human EKP-1 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire EPK-55053 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the EPK-55053 DNA sequence is amplified by PCR using two primers. The 5' primer contains the restriction site of interest followed by approximately twenty nucleotides of the EPK-55053 coding sequence starting from the initiation codon; the 3' end sequence contains complementary sequences to the other restriction site of interest, a translation stop codon, the HA tag or FLAG tag and the last 20 nucleotides of the EPK-55053 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the EPK-55053 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the EPK-55053-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J. et al., *Molecular Cloning: A Laboratory Manual*. 2nd ed. Cold Spring Harbor Laboratory, Cold Spring Harbor Laboratory Press, Cold Spring Harbor, N.Y., 1989. The expression of the EPK-55053 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the EPK-55053 coding sequence is cloned directly into the polylinker of the pCDNA/Amp vector using the appropriate restriction sites. The resulting plasmid is transfected into COS cells in the manner described above, and the expression of the EPK-55053 polypeptide is detected by radiolabeling and immunoprecipitation using an EPK-55053 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   (a) a nucleic acid molecule comprising the nucleotide sequence set forth in SEQ ID NO:1, or a complement thereof; and
   (b) a nucleic acid molecule comprising the nucleotide sequence set forth in SEQ ID NO:3, or a complement thereof.

2. An isolated nucleic acid molecule which encodes a polypeptide comprising the amino acid sequence set forth in SEQ ID NO:2, or a complement thereof.

3. An isolated nucleic acid molecule comprising the nucleic acid molecule of any one of claims 1, or 2 and a nucleotide sequence encoding a heterologous polypeptide.

4. A vector comprising the nucleic acid molecule of any one of claims 1, or 2.

5. The vector of claim 4, which is an expression vector.

6. A host cell transfected with the expression vector of claim 5.

7. A method of producing a polypeptide comprising culturing the host cell of claim 6 in an appropriate culture medium to, thereby, produce the polypeptide.

8. A kit comprising a compound which selectively hybridizes to a complement of the nucleic acid molecule of any one of claims 1, or 2 and instructions for use.

* * * * *